(12) United States Patent
Brown et al.

(10) Patent No.: US 7,130,677 B2
(45) Date of Patent: Oct. 31, 2006

(54) METHODS AND APPARATUS FOR DISCRIMINATING POLYMORPHIC TACHYARRHYTHMIAS FROM MONOMORPHIC TACHYARRHYTHMIAS FACILITATING DETECTION OF FIBRILLATION

(75) Inventors: Mark L. Brown, North Oaks, MN (US); Shantanu Sarkar, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 551 days.

(21) Appl. No.: 10/653,000

(22) Filed: Aug. 29, 2003

(65) Prior Publication Data

US 2004/0111121 A1    Jun. 10, 2004

Related U.S. Application Data

(60) Provisional application No. 60/430,926, filed on Dec. 4, 2002.

(51) Int. Cl.
*A61B 5/046* (2006.01)
(52) U.S. Cl. ............................... 600/515; 607/4; 607/5
(58) Field of Classification Search .................... 607/4, 607/5, 14; 600/515–518
See application file for complete search history.

(56) References Cited

U.S. PATENT DOCUMENTS

| | | | |
|---|---|---|---|
| 4,552,154 A | 11/1985 | Hartlaub | |
| 5,086,772 A | 2/1992 | Larnard et al. | |
| 5,193,535 A | 3/1993 | Bardy et al. | |
| 5,240,009 A | 8/1993 | Williams | |
| 5,312,441 A | 5/1994 | Mader et al. | |
| 5,331,966 A | 7/1994 | Bennett et al. | |
| 5,342,402 A | 8/1994 | Olson et al. | |
| 5,379,776 A | 1/1995 | Murphy et al. | |
| 5,400,795 A | 3/1995 | Murphy et al. | |
| 5,439,483 A | 8/1995 | Duong-Van | |
| 5,447,519 A | 9/1995 | Peterson | |
| 5,545,186 A | 8/1996 | Olson et al. | |
| 5,645,070 A | 7/1997 | Turcott | |
| 5,782,876 A | 7/1998 | Flammang | |
| 5,797,399 A | 8/1998 | Morris et al. | |

(Continued)

FOREIGN PATENT DOCUMENTS

WO    WO 01/80042 A1    10/2001

OTHER PUBLICATIONS

Wilkoff et al. "Critical Analysis of Dual-Chamber Implantable Cardioverter-Defibrillator Arrhythmia Detection: Results and Technical Considerations" *Circulation.* 2001;103:381-6.

*Primary Examiner*—Robert Pezzuto
*Assistant Examiner*—Yun Haeng Lee
(74) *Attorney, Agent, or Firm*—Michael C. Soldner; Girma Wolde-Michael

(57) ABSTRACT

Methods and apparatus are provided for discriminating high rate polymorphic QRS complexes from high rate monomorphic QRS complexes to increase the specificity of detection of polymorphic VT and VF employing wavelet transform signal processing of the QRS complexes are disclosed. Wavelet transforms are applied to the sampled amplitude values of a sequence of QRS complexes to develop wavelet transform coefficient (WTC) data sets. At least selected ones of the WTC data sets are processed and comparisons are made to determine a wavelet match score. A determination is made as a function of the wavelet match scores of the series of successive QRS complexes that characterizes the most recent QRS complex as more or less likely to signify polymorphic VT or VF.

42 Claims, 6 Drawing Sheets

U.S. PATENT DOCUMENTS

| | | |
|---|---|---|
| 5,810,739 A | 9/1998 | Bornzin et al. |
| 5,814,079 A | 9/1998 | Kieval |
| 6,212,428 B1 | 4/2001 | Hsu et al. |
| 6,266,554 B1 | 7/2001 | Hsu et al. |
| 6,275,732 B1 | 8/2001 | Hsu et al. |
| 6,393,316 B1 | 5/2002 | Gillberg et al. |
| 6,745,068 B1 | 6/2004 | Koyrakh et al. |
| 2002/0019593 A1 | 2/2002 | Hsu et al. |
| 2002/0032469 A1 | 3/2002 | Marcovecchio |
| 2002/0193695 A1 | 12/2002 | Koyrakh et al. |
| 2004/0088013 A1 | 5/2004 | Stadler et al. |

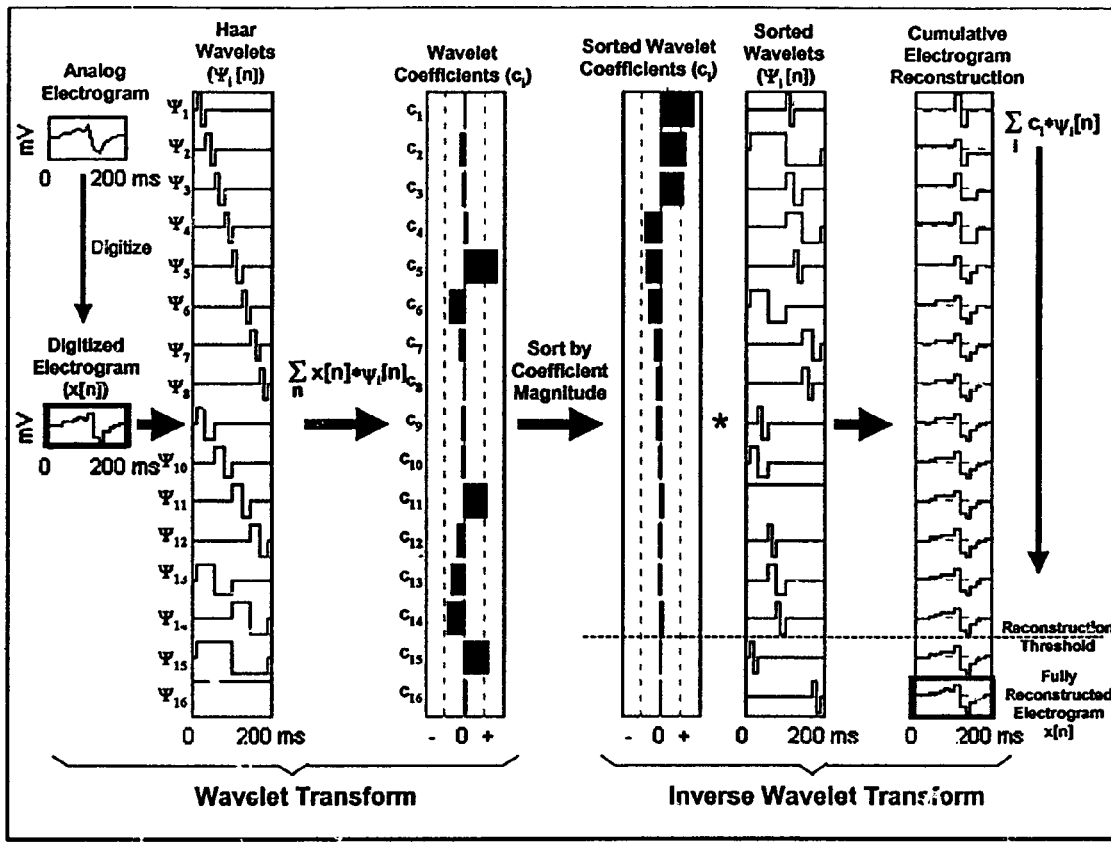
FIG. 5
FIG. 6
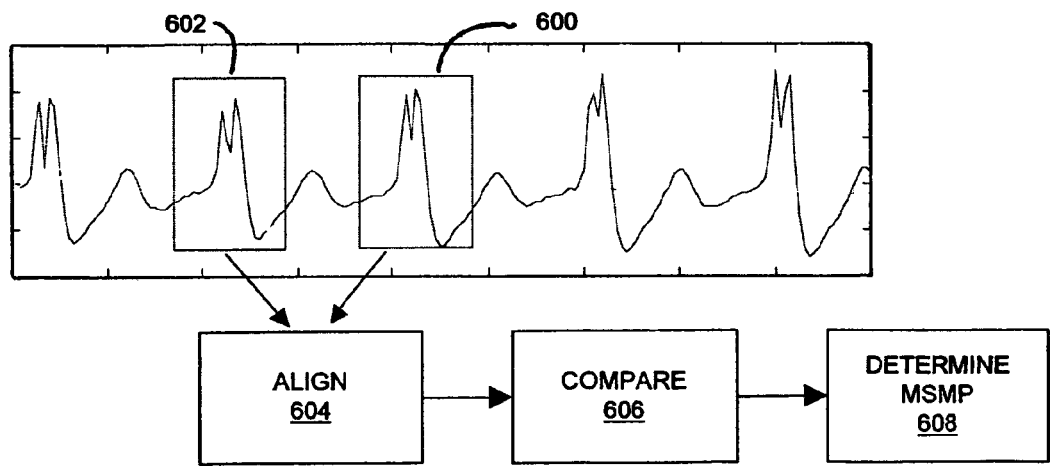

METHODS AND APPARATUS FOR DISCRIMINATING POLYMORPHIC TACHYARRHYTHMIAS FROM MONOMORPHIC TACHYARRHYTHMIAS FACILITATING DETECTION OF FIBRILLATION

RELATED APPLICATIONS

This application claims priority to provisional U.S. Application Ser. No. 60/430,926, filed Dec. 4, 2002.

This application is related to U.S. patent application Ser. No. 10/652,757 filed on even date herewith for METHODS AND APPARATUS FOR DISCRIMINATING POLYMORPHIC TACHYARRHYTHMIAS FROM MONOMORPHIC TACHYARRHYTHMIAS FACILITATING DETECTION OF VENTRICULAR FIBRILLATION and to U.S. patent application Ser. No. 10/652,695 filed on even date herewith for METHODS AND APPARATUS FOR DISCRIMINATING POLYMORPHIC TACHYARRHYTHMIAS FROM MONOMORPHIC TACHYARRHYTHMIAS FACILITATING DETECTION OF VENTRICULAR FIBRILLATION, both filed in the names of Shantanu Sarkar et al.

FIELD OF THE INVENTION

This invention relates to implantable medical devices (IMDs), and more particularly to improved methods and apparatus for discriminating among tachyarrhythmias in implantable heart monitors and cardiac stimulators, such as implantable cardioverter/defibrillators (ICDs).

BACKGROUND OF THE INVENTION

By way of definition, the heart is said to be in normal sinus rhythm (NSR) when the atria and ventricles beat in synchrony at a heart rate lower than a defined tachycardia heart rate that provides sufficient cardiac output of oxygenated blood to the body at rest and during exercise or stress. The term bradycardia refers to an abnormal slow rate of one or more heart chamber that inappropriately provides insufficient cardiac output at rest or during stress or exercise. The term "tachyarrhythmia" refers to any abnormal fast rhythm of one or more heart chamber that reduces cardiac output and may be amenable of conversion to NSR by "cardioversion" or "defibrillation" or the application of certain anti-tachycardia pacing therapies to the heart chamber as described further herein. Atrial tachyarrhythmias include atrial tachycardia (AT) and atrial flutter or fibrillation (AF) originating from one or more ectopic sites in the right or left atria. Ventricular tachyarrhythmias include ventricular tachycardia (VT) and ventricular flutter or fibrillation (VF) originating from one or more ectopic sites in the ventricles. Supraventricular tachycardia (SVT) can also result from high rate atrial tachyarrhythmias or junctional depolarizations conducted to the ventricles including AV re-entrant tachycardia, which usually conducts down the AV node and up through left postero-lateral bypass tract is considered an SVT. Individuals whose hearts go into VF or into high rate, polymorphic VT can suffer sudden cardiac death (SCD) unless the rhythm terminates either spontaneously or therapeutically within a very short time after onset of such high rate VT or VF.

AF and VF are characterized by chaotic electrical activity that exhibits highly variable depolarization wavefronts that are propagated in directions that differ from the directions of propagation during NSR and more rhythmic tachycardias. The depolarization waves traversing the atria during AF and the ventricles during VF do not follow normal conduction pathways and can vary in direction from beat to beat. During AF and VF episodes (particularly at onset and during the initial phase before cardiac activity diminishes), the depolarization waveforms are irregular in amplitude and hence in appearance when viewed on an electrocardiogram strip or display and are characterized as "polymorphic". In addition, the atrial or ventricular EGM does not exhibit a characteristic baseline of little electrical activity separating P-waves or QRS complexes, respectively.

The QRS complexes of rhythmic atrial and ventricular tachycardia episodes typically exhibit a regular or "monomorphic" P-waves or QRS waveforms that simply become narrower as heart rate increases from NSR and that are separated by a baseline interval. However, the QRS complexes during certain VT episodes can be polymorphic, particularly from one beat to the next. Such polymorphic VT episodes may be due to reentry conduction through diseased tissue, which results in QRS depolarization wavefronts that are also typically propagated in directions that differ from those prevalent during NSR or monomorphic VT or SVT episodes.

In the field of automatic implantable arrhythmia control devices, particularly ICDs (also referred to as pacemaker/cardioverter/defibrillators or PCDs), the terms "cardioversion" and "cardioverter" and "defibrillation" and "defibrillator" generally refer to the processes of and devices for discharging relatively high energy electrical shocks into or across cardiac tissue to arrest a life threatening tachyarrhythmia. In practice, the conversion of AT or VT or low rate AF or VF to normal sinus rhythm by a relatively low amplitude cardioversion shock delivered in timed synchrony with a sensed atrial or ventricular cardiac depolarization (P-wave or R-wave) is typically referred to as "cardioversion". The conversion of malignant AF or VF by the same or higher energy shock delivered without requiring such synchronization is typically referred to as "defibrillation". Synchronization can be attempted, but therapy is delivered without synchronization if synchronization is not possible in a short time. Cardioversion shocks that may or may not be synchronized with a cardiac depolarization or rhythm and may be applied to arrest a VT with a lower range energy pulse of around 1–15 Joules or VF with a medium to high energy pulse of 7–40 Joules, nominally. In the following description and claims, it is to be assumed that the terms cardioversion and defibrillation are interchangeable, and that use of one term is inclusive of the other, unless specific distinctions are drawn between them in the context of the use. For convenience, cardioversion and/or defibrillation shocks or shock therapies are referred to herein as C/D shocks or shock therapies.

Bradycardia cardiac pacing functions are also currently incorporated into ICDs to supplant some or all of an abnormal heart's natural pacing function by delivering appropriately timed pacing pulses to cause a chamber or chambers of the heart to contract or "beat", i.e., to "capture" the heart. Either single chamber (atrial or ventricular) pacing functions or dual chamber (atrial and ventricular) pacing pulses are applied to the atria and/or the ventricles in response to bradycardia or dissociation of the atrial and ventricular heart rates at a pacing rate to restore cardiac output that is appropriate to the physiologic requirements of the patient. Most recently, synchronized right and left heart pacing, particularly synchronized pacing of the right and left ventricles, has been incorporated into ICDs for heart failure patients who are also susceptible to tachyarrhythmias.

In addition, anti-tachycardia pacing capabilities have been incorporated into ICDs for delivering bursts of pacing pulses or single overdrive pacing pulses to the atria and/or the ventricles to counter and convert certain slow AT or VT episodes to normal sinus rates. The number, frequency, pulse amplitude and width of burst pacing pulse therapies can be programmed by remote programming and telemetry equipment to meet physiologic needs of the particular patient and power conservation requirements.

Among the most important functions of such ICDs are to detect tachyarrhythmias, to correctly identify the tachyarrhythmia, to supply an appropriate cardioversion/defibrillation or burst pacing therapy, and to determine whether or not the supplied therapy was effective.

The typical VT and VF detection criteria that have been employed in commercially released ICDs employ rate/interval based timing criterion and duration or frequency criterion as a basic mechanism for detecting the presence of and distinguishing between tachyarrhythmias. To this end, the intrinsic heart rate is measured on a beat-to-beat basis by timing the R—R interval between successive ventricular sense (VSENSE) event signals output by an R-wave sense amplifier. The measured R—R intervals are compared to a fibrillation detection interval (FDI), a fast tachycardia detection interval (FTDI) and a slow tachycardia detection interval (TDI), and respective VF, fast VT or slow VT counts are accumulated depending on the result of the comparison. One of VF, fast VT or slow VT is declared when a count matches a particular number of intervals required for detection (referred to herein as "NID"). Each rate zone may have its own defined NID, for example, "VFNID" for fibrillation detection, "FVTNID" for fast VT detection, and "VTNID" for slow VT detection.

For example, the measured R—R intervals are compared to the FDI criterion, and the ventricular sensed event is declared a VF event or a non-VF event depending upon the results of the comparison. VF is provisionally declared when the count meets (i.e., equals or exceeds) the VFNID frequency criterion. Similarly, the ventricular sensed event can be declared a fast VT or a slow VT depending on the results of the comparison to the FTDI and the TDI.

Often, SVT episodes causing the ventricles to beat at a rate that meets the FDI and can be inappropriately detected as VF episodes. In ICDs having dual chamber, atrial and ventricular, sensing capabilities, further strategies have been generally followed to detect and classify atrial and ventricular tachyarrhythmias. Algorithms have been developed that identify atrial sensed events from P-waves and/or ventricular sensed events from R-waves and derive atrial and/or ventricular event intervals and/or rates therefrom. Various detection and classification systems have been proposed as set forth in commonly assigned U.S. Pat. Nos. 5,342,402, 5,545,186, 5,782,876, and 5,814,079, that invoke a hierarchy of prioritization rules to make a decision as to when a cardioversion/defibrillation therapy is to be delivered or withheld. These rule-based methods and apparatus have been incorporated in dual chamber ICDs to distinguish atrial and ventricular tachyarrhythmias employing "PR logic" in dual chamber MEDTRONIC® GEM® DR ICDs.

Single chamber ICDs for distinguishing VF from VT or SVT and providing ventricular C/D shock therapies and/or burst pacing therapies do not have the capabilities of sensing P-waves to detect atrial sensed events and analyzing the relationship between atrial sensed events and ventricular sensed events based on detected R-waves. Therefore, many other proposals have been made to examine electrogram (EGM) waveform characteristics, particularly unique waveform characteristics of the QRS complex during NSR, VT, VF and SVT.

One method of discriminating between VF and NSR EGM waveforms as set forth in commonly assigned U.S. Pat. No. 5,312,441, for example, is based on measurements and comparisons of the width of the QRS complex to VF width criterion. A normal QRS complex is generally narrower than the abnormal QRS complex during VF, and so QRS width can be employed to distinguish the normal QRS complex from the abnormal QRS complex during VF. However, there are cases when an abnormal QRS complex during VT will have a different morphology than the normal QRS complex while remaining narrow. Conversely, the QRS complex during certain SVT episodes can also be wide. In those cases, a more sensitive and selective method is needed to discriminate between different waveforms.

As noted above, ORS depolarization waves traversing the ventricles during VF do not follow normal conduction pathways and can vary in direction from beat to beat, whereas QRS depolarization waves during SVT that follow normal conduction pathways or during VT emanating from stable ectopic depolarization sites do not vary significantly in direction of propagation. Therefore, various proposals have been made to distinguish VF from a stable VT or SVT as a function of the QRS wave propagation direction on a beat-to-beat basis.

The VT/VF discriminator disclosed in commonly assigned U.S. Pat. No 5,193,535 employs two sense electrode pairs, e.g., a near field or bipolar electrode pair and a far field or unipolar electrode pair, that are coupled to detection circuitry for identifying the points in time when the sensed electrical signals resulting from the passage of a depolarization wavefront (ORS complex) meet certain predetermined criteria, hereafter referred to as the first and second "fiducial points", that may or may not be the same. The cumulative variability of the time intervals separating the occurrence of the first and second fiducial points over a series of R—R intervals that satisfy VF or VT detection criteria is determined. In general terms, the cumulative variability of a series of true VF QRS complexes resulting in satisfaction of VF detection criteria is higher than the cumulative variability of a series of stable VT QRS complexes or SVT QRS complexes satisfying the VF detection criteria. The cumulative variability value or index is used to distinguish VF from high rate VT to trigger or withhold delivery of a C/D shock therapy. Similar techniques are disclosed in U.S. Pat. No. 5,810,739.

A further approach to the discrimination of normal heart beats from abnormal heart beats employing the morphology of the QRS complex is based on making a comparison of the waveform of the QRS complex during tachyarrhythmia with the waveform of a "template" recording of a QRS complex in NSR and optionally, other template recordings made during VF or VT. An ICD is disclosed in commonly assigned U.S. Pat. No. 5,447,519 that discriminates between monomorphic ventricular tachyarrhythmias, particularly VT, from polymorphic ventricular tachyarrhythmias, particularly VF. A fiducial point of each successive QRS complex is detected (e.g., a VSENSE) prompting the storage of sampled and digitized waveform amplitude data within a timing window bridging the point in time of fiducial point detection. Stored sets of such sampled wave shape data are compared data point to data point resulting in a sampled morphology index value for each compared set. The magnitude of the sampled morphology index value or a series such index values are analyzed to determine the presence of a single or a progression of beat-to-beat waveform changes indicative of a polymorphic single transition or progression of QRS complexes from monomorphic to polymorphic waveforms indicative of an arrhythmia that should be treated with aggressive C/D shock therapies. The ICD is preferably provided with a closely spaced and widely spaced pairs of electrodes for sensing each QRS complex as in the above-referenced '535 patent. The closely spaced electrode pair is coupled to sense detect circuitry for identifying the fiducial point and to counting and comparison circuitry for developing rate and onset data. The widely spaced pair of electrodes is coupled to sense and digitizing circuitry for developing the sampled waveform amplitude data from which the morphology index values are derived.

The common approach for such morphology analysis is Correlation Waveform Analysis (CWA) or its less computationally costly counterpart, so-called Area of Difference (AD) analysis. Both require minimization of a function describing difference between two signals (sum of squared differences of wave data points for the case of CWA, and the sum of absolute values of the differences for AD analysis). However, such computations, as typically performed, are more computationally costly and consume more power to carry out than is generally desirable within ICDs.

As set forth in the U.S. Pat. No. 5,439,483, a great deal of information for characterizing the EGM signal, particularly the ORS complexes, if the information can be extracted and analyzed employing mathematical transforms. The Fourier transform is most commonly employed in waveform analysis to find the probability of any individual frequency occurring in the waveform. In this way, a time varying signal is represented as the sum of its frequencies. A large amount of data from a signal may be compressed, and certain information that may be hidden in the data may be viewed from a different perspective. The power of this representation diminishes when the signal that one is trying to represent changes its character unpredictably during the course of the signal. Essentially, local information is lost when the global representation of a Fourier transform is attempted.

As asserted in the '483 patent, an improved method of performing this type of transform is known as the windowed Fourier transform, wherein the time series is divided into small windows in time or in space depending on the nature of the data. The transform is performed to obtain the Fourier spectra of the data at various windows. The problem with this technique is that the uncertainty principle begins to set in. The smaller the window, so designed to better handle the localization of the data, the worse its frequency information becomes. The uncertainty principle can be minimized using the Gabor transform, which makes use of the theorem that the minimum uncertainty is achieved with the Gaussian window. Thus, a Gaussian function is used instead of performing the transform to break the signal down into its basic frequencies represented by a time series of sine and cosine functions. This improves the Fourier transform but still cannot give the detailed information of the time series.

Uses of the Haar wavelet transform for performing morphologic analysis and discrimination of normal and abnormal QRS complexes is described in the above-referenced '483 patent and in commonly assigned U.S. Pat. No. 6,393,316. Wavelets represent a signal in a way that provides local frequency information for each position within the signal or digitized sample of the signal amplitude, as described in detail in the '316 patent. Thus, the wavelet transform can be used to extract information of the time series that is not restricted to the sine or cosine functions of the Fourier transform. Essentially, any function can be chosen that is appropriate for obtaining the relevant information of the time series. The advantage is that the signal can be observed at any time scale, i.e., the technique can zoom in on the signal, up to its finest resolution. As set forth in the above-referenced '316 patent, the wavelet transform is a representation of a signal as a sum of so-called wavelets or little waves. The wavelets are highly localized in time or, in the mathematical language, have compact support. The main difference between the wavelet functions used in wavelet transforms and the sine and cosine functions used in the Fourier transform is that families of wavelets have limited time support that scales exponentially.

There are certain computational advantages of using wavelet transforms instead of Fourier transforms as described in detail in the above-referenced '316 patent. The wavelet transform applied to digitized QRS amplitude sample values will yield a set of wavelet transform coefficient (WTC) data, and a selected sub-set of the WTC data can be employed to accurately represent the QRS complex, and thus will achieve a high degree of information compression. This can be especially important for IMDs because the information compression provided can be employed to substantially reduce the number of required computations. The ORS signal can also be efficiently filtered and de-noised by keeping a number of large amplitude wavelet coefficients and deleting lower amplitude wavelet coefficients. Thus, the use of a wavelet transform-based morphology analysis method significantly reduces the amount of computation necessary to perform the task and performs de-noising of the signal at no additional computational cost.

The above-referenced '483 patent discloses a system and method for characterizing the "seriousness" of a VF episode using wavelet transforms of each QRS complex in a series of QRS complexes, so that a C/D shock may be delivered to the ventricles with an appropriate amount of energy. A wavelet transform of the second derivative of the time series of a fibrillation event is performed on digitized QRS complexes in the EGM to provide spectral functions of the QRS complexes. In the algorithm disclosed in the '483 patent, the results are analyzed for "missing peaks" in the data. The more serious the VF, the more peaks will be missing from the data. This information may then used to modify the energy of the C/D shock as a function of the estimated seriousness of the VF.

The above-referenced '316 patent discloses a method and apparatus for reliable discrimination between ventricular depolarizations resulting from normal and abnormal propagation of depolarization wavefronts through the chambers of a patient's heart by means of a Haar wavelet transform-based method of analysis of QRS complexes of the EGM. Several embodiments are described in the '316 patent that involve the development of WTC templates of NSR as well as SVT QRS complexes and comparison of current high rate QRS complexes satisfying VT or VF rate criteria to the stored WTC templates. A first disclosed embodiment compares template and unknown waveforms in the wavelet domain by ordering WTC data of the template and unknown waveforms by absolute amplitude and comparing the resulting orders of the WTC data. The second and third disclosed embodiments perform analogs of CWA and AD computations in the wavelet domain. All three methods produce good discrimination of QRS complexes during VT episodes from normal QRS complexes during SVT episodes and may be readily implemented in the embedded environments of ICDs. It is asserted that the disclosed embodiments may also be usefully applied to discriminate between other cardiac waveforms in the EGM, including normal atrial P-waves and those associated with atrial AF and AT episodes. Certain features of the wavelet morphology algorithms disclosed in the '316 patent are employed in the single chamber MEDTRONIC® Marquis® VR ICDs.

Both the complexity and the indications for implantation of the above-described ICDs have increased remarkably over the years. Patients who receive such ICDs are typically identified as survivors of SCD secondary to VF that may originate as VT. In such cases, the cost and complexity of such ICDs is deemed warranted. However, many patients likely to suffer SCD are presently un-diagnosed and do not survive their first VF episode. It is believed that certain patient populations exist that could be identified from other indicia and could benefit from a "prophylactic", low cost, limited function, ICD that simply provides protection against SCD due to VF. To minimize cost of the ICD and the implantation procedure, such a prophylactic ICD would necessarily have limited functions and the capability of delivering only a limited number of high-energy C/D shocks in response to a detected VF episode.

In a prophylactic ICD application, there is concern that the selected patients will exhibit nearly the same frequency of SVT episodes but far fewer polymorphic VT or VF episodes than is exhibited by the conventional ICD patient population. Therefore, it is feared that the use of the current VF detection algorithms will result in a higher percentage of inappropriate VF shock therapies than in the conventional ICD population. This is expected because Bayes' theorem teaches that detection performance depends not only on the detection algorithm's intrinsic performance, but also depends on the population of tachyarrhythmias that the algorithm processes.

In the prophylactic ICD application, AF episodes that conduct rapidly to the ventricle (rapidly conducted AF) are of particular concern. The ventricular rate of such AF events is often similar to that of VF and very hard to discriminate from simultaneous AF and VTNF on the basis of intervals alone. Wilkoff et al. identified rapidly conducted AF as one of the primary algorithmic causes for inappropriate VTNF detection in dual-chamber ICDs. In a single chamber detection scenario for a wider population, as in the case of prophylactic ICDs, it is expected that rapidly conducted AF that conducts at ventricular rates that overlap with the VF zone will also be a primary algorithmic cause for inappropriate detection. See, Wilkoff B. L. et. al., "Critical Analysis of Dual-Chamber Implantable Cardioverter-Defibrillator Arrhythmia Detection: Results and Technical Consideration", *Circulation*, 2001; 103:381–386.

The QRS morphology during rapidly conducted AF often differs from the QRS morphology during NSR rendering algorithms that rely on a finding of similarity between the current QRS complex morphology and an NSR QRS complex morphology to distinguish SVT from VF much less effective. Although the QRS morphology during AF episodes differs from NSR QRS morphology, there is often a characteristic QRS complex morphology during AF that is relatively stable over short periods of time.

Therefore, a need remains for a robust and computationally efficient VF detection capability of discriminating a true VF episode from high rate VT or SVT that is not life threatening particularly for use in prophylactic ICDs to avoid the unnecessary delivery of a C/D shock therapy. Such a VF detection capability would, of course, still be beneficial in more complex single chamber, dual chamber and multi-chamber ICDs. Such a robust VF detection capability may also find utility in an implantable heart monitors (IHM) having a sense electrode array (SEA) implanted subcutaneously for monitoring, processing, and storing data from the EGM sensed across one or more selected far field sense vector as described in commonly assigned U.S. Pat. No. 5,331,966, for example.

Moreover, a need remains for a robust and computationally efficient AF detection capability of discriminating a true AF episode from high rate AT.

SUMMARY OF THE INVENTION

In accordance with the present invention, methods and apparatus are provided for discriminating high rate polymorphic QRS complexes from high rate monomorphic QRS complexes to increase the specificity of detection of polymorphic VT and VF from other rapid ventricular contractions that can result from AF that is rapidly conducted to the ventricles resulting in R—R intervals that satisfy VTNF rate detection criterion. In particular, methods and apparatus are provided that robustly distinguish polymorphic VT or VF originating in the ventricles from a monomorphic VT that may be due to rapidly conducted AF. The present invention is preferably employed in a prophylactic single chamber ICD or in a more complex single chamber, dual chamber or multi-chamber ICD or in cardiac monitors.

In an exemplary ICD embodiment, the methods and apparatus of the present invention augment VF detection criteria by determining if a predetermined number of high rate QRS complexes resulting in detected ventricular sense events and satisfying the VF detection criteria are monomorphic or polymorphic. The delivery of the C/D shock that would be delivered based on satisfaction of the VF detection criteria is withheld, and an anti-tachycardia therapy may be delivered if the predetermined number of the QRS complexes are monomorphic. In other words, a sequence of high rate QRS complexes that satisfied the VF detection criteria are deemed to be more likely due to VT or SVT than due to VF if at least a number of the QRS complexes are determined to be monomorphic. In an embodiment that further increases specificity, delivery of the C/D shock is postponed by a withhold delay number (e.g., z) of subsequent ventricular sensed events each time that a QRS complex is examined and the predetermined number of QRS complexes are found to be monomorphic.

Preferred embodiments of the present invention use a measure of the morphologic stability of the QRS complexes as a supplementary VF discriminatory criterion to aid in discrimination of polymorphic VF and VT from monomorphic VT and SVT. Particular algorithms of the present invention that determine morphologic stability of the QRS complexes are titled the Two Beat Match Percent stability (2 bMP) algorithm, the Multiple Beat Match Percent stability (mbMP) algorithm, and the selective wavelet coefficient stability index (SWCSI). In general, wavelet transforms are applied to the sampled amplitude values of the y QRS complexes to develop y sets of WTC data. At least selected ones of the sets of WTC data are processed and comparisons are made sequentially or simultaneously to determine a set of morphologic stability match percent values. Each morphologic stability match percent is compared to a match threshold, and a match count is incremented or decremented when a morphologic stability match percent meets or does not meet, respectively, the match threshold. The match count is compared to a count threshold, and the QRS complexes are deemed to be more or less likely to signify polymorphic VT or VF depending upon the results of the comparison.

Advantageously, detection of VF and the discrimination of VF from VT and SVT is made more robust and specific.

The frequency of false VF declarations and inappropriate deliveries of C/D shocks is lowered, particularly in prophylactic ICDs. The invention may also be applied to discriminate atrial tachyarrhythmias, particularly AF from AT.

This summary of the invention has been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein:

FIG. 5 is a graphical illustration of wavelet transform signal processing of a QRS complex to develop a WTC data set;

FIG. 6 is a graphical depiction of the 2 bMP algorithm that can be practiced in the flow chart of FIGS. 3 and 4;

DETAILED DESCRIPTION OF THE PREFERRED EMBODIMENTS OF THE INVENTION

In the following detailed description, references are made to illustrative embodiments of methods and apparatus for carrying out the invention. It is understood that other embodiments can be utilized without departing from the scope of the invention. In particular, the present invention is described in the context of a simple single chamber ICD for providing the functions of monitoring the ventricular EGM, detecting VF, VT and SVT, discriminating VF from VT and SVT, and providing a C/D shock in response to a detected VF episode, storing data related to detected VF, VT and SVT episodes for uplink telemetry transmission to external medical devices, and optionally providing VVI pacing for bradycardia. The preferred embodiment can advantageously be simplified to function as a prophylactic ICD without pacing capabilities that provides unsynchronized, high energy, C/D shocks upon detection of VF episodes in anticipation that the patient will thereby survive such VF episodes and be a candidate for implantation of a more complex ICD. However, it will be appreciated from the following that the various embodiments and principles of the present invention may be employed and practiced in an IHM for simply monitoring the ventricular EGM, detecting VF, VT, and SVT, discriminating VF from VT and SVT, and storing data related to detected VF episodes for uplink telemetry transmission to external medical devices or practiced in more complex tiered therapy delivery, dual chamber or multi-chamber ICDs.

Figure 1:
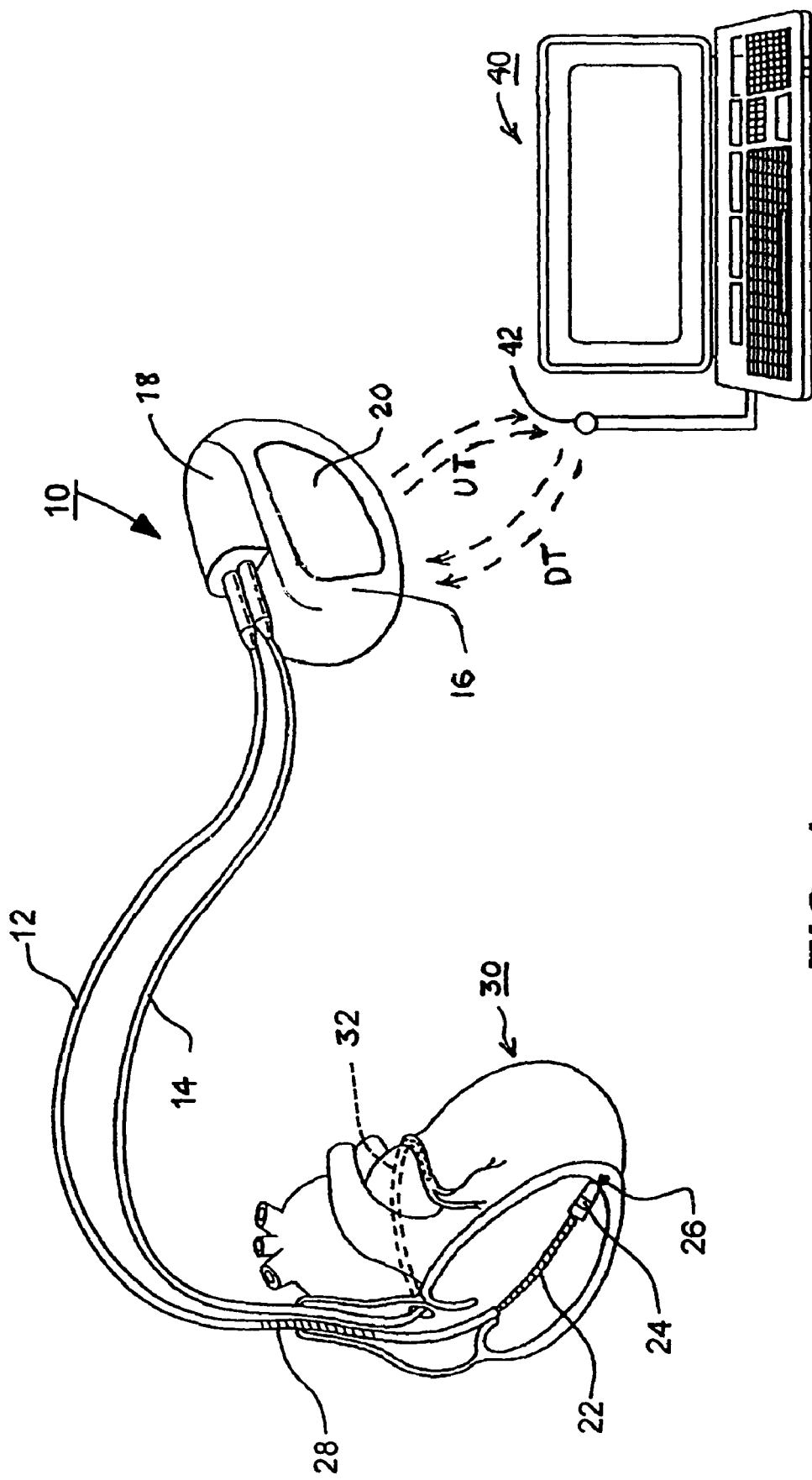
FIG. 1 is a schematic illustration of an ICD IPG and associated ICD leads extending from the ICD IPG to C/D and pace/sense electrodes located in operative relation to the ventricles of a heart.

FIG. 1 illustrates one embodiment of an ICD comprising an ICD implantable pulse generator (IPG) 10 in which the discrimination algorithms of the present invention can be advantageously incorporated and the associated ICD medical electrical leads 12 and 14 extending to a human heart 30. The ICD of FIG. 1 is also shown in relation to an external programmer 40 and external programmer telemetry antenna 42 providing uplink telemetry (UT) and downlink telemetry (DT) transmissions with an IPG antenna.

Figure 2:
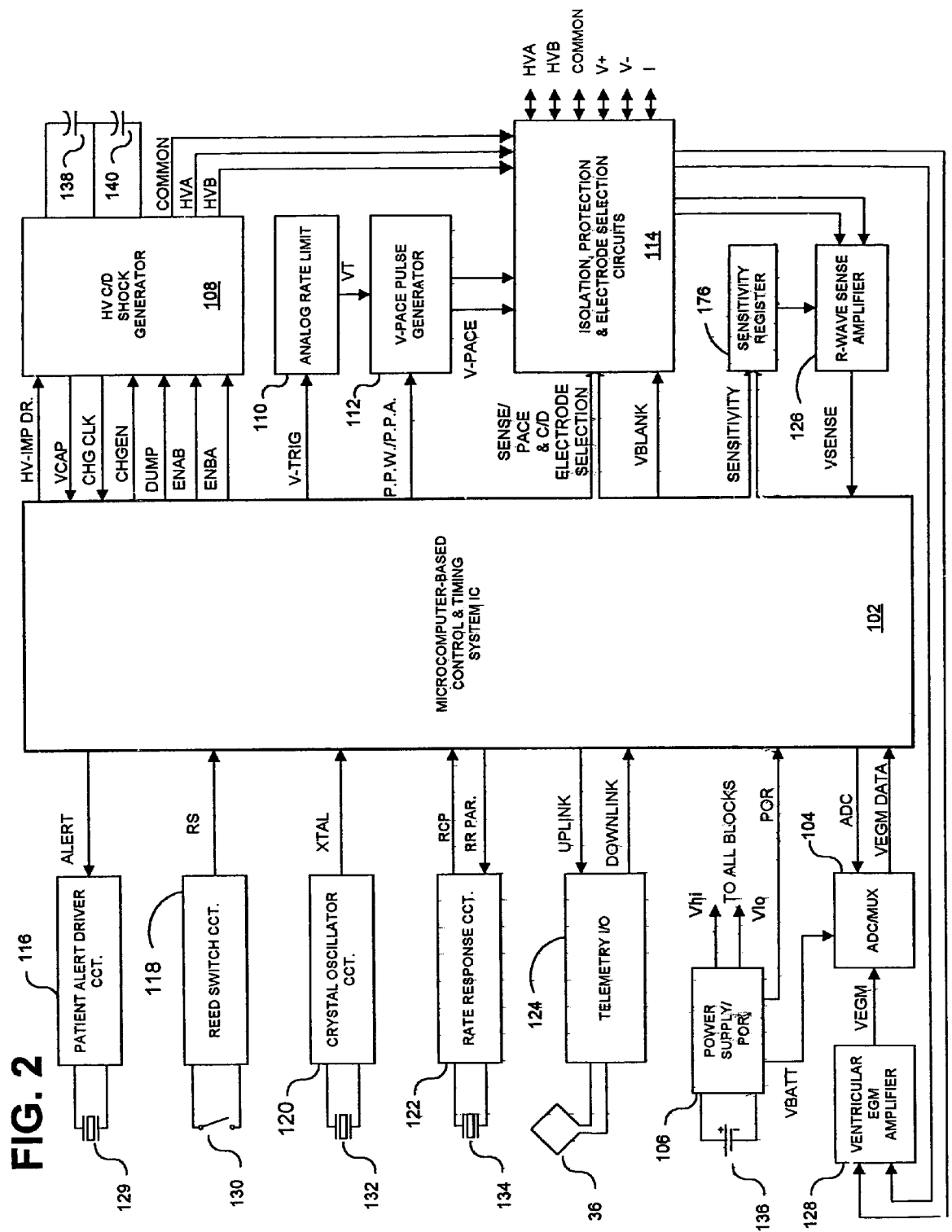
FIG. 2 is a schematic block diagram of the circuitry of the ICD IPG of FIG. 1 in which the present invention may advantageously be practiced.

The ICD IPG 10 is formed of a hermetically sealed enclosure 16 containing the electronic circuitry and components, including a battery, depicted in FIG. 2 and a connector block 18. The proximal ends of the illustrated ICD leads 12 and 14 are inserted into two connector ports of the connector block 18 to make electrical connections between lead conductors of the ICD leads 12 and 14 and the circuitry within the hermetically sealed enclosure 16 via feedthroughs extending through the enclosure wall in a manner well known in the art.

The ICD IPG 10 is intended to be implanted subcutaneously remote from the heart, and at least an uninsulated portion of the hermetically sealed enclosure 16 may be employed as an indifferent pace/sense and/or C/D electrode 20. The ICD lead 14 and the ICD lead 12 are a coronary sinus (CS) lead and a right ventricular (RV) lead, respectively that are extended transvenously from the ICD IPG 10 into the heart chambers using conventional implantation techniques.

The CS lead 14 supports an elongated wire coil, C/D electrode 32 that is located in the coronary sinus and great vein region of the heart 30. The C/D electrode 32 is advanced through the coronary sinus ostium in the right atrium and around the heart, and is disposed in proximity with the left ventricular wall either in the great vein or in the coronary sinus.

The RV lead 12 supports proximal and distal, elongated wire coil, C/D electrodes 22 and 28, a ring-shaped pace/sense electrode 24, and a helical pace/sense electrode 26 comprising an active fixation helix. The helical pace/sense electrode 26 is screwed into the tissue of the right ventricle at the right ventricular apex to fix the pace/sense electrodes 24 and 26 in the right ventricle. Other RV fixation mechanisms well known in the art, e.g., soft, pliant tines, may be substituted for the active fixation helix.

The C/D electrodes 22 and 28 are disposed in the RV and superior vena cava (SVC) respectively to define one C/D vector between the base and apex of the heart 30. An RV-LV C/D vector is defined between the C/D electrodes 22 and 32. Other C/D vectors can be defined between the subcutaneous housing electrode 20 and any of the C/D electrodes 22, 28 and 32. Pairs of the C/D electrodes 22, 28 and 32 can be selectively coupled together to define further C/D vectors in a manner known in the art.

In conjunction with the present invention, the illustrated ICD leads and described electrodes are merely exemplary of possible lead systems and electrodes that can be paired together to detect R-waves, to process the EGM, to deliver C/D shocks in response to a confirmed VF detection, and to provide pacing, particularly to the RV. The illustrated ICD leads and electrodes provide a variety of sense electrodes that can be paired and coupled to a ventricular sense amplifier to detect R-waves, an EGM amplifier to sense the EGM, and to a C/D shock generator to deliver monophasic or biphasic C/D shocks to the heart to counter VF. It will be understood that other ICD leads and pace/sense and C/D electrodes can be employed in the practice of the invention as long as the electrodes provide sense electrode pairs for detection of R-waves, for sensing the EGM, and for delivering the monophasic or biphasic C/D shocks to the heart to counter VF.

For example, in the simplest case of a low cost, limited function, prophylactic ICD, the ICD leads may comprise a simpler RV lead supporting only the C/D electrode 22 and a single distal pace/sense electrode or a bipolar pair of distal pace/sense electrodes. A high energy C/D shock can be delivered between the C/D electrode 22 and the housing C/D electrode 20. The R-waves and the EGM can be sensed between the selected pace/sense electrode pairs. RV pacing during bradycardia may or may not be provided between a selected pace/sense electrode pair.

Returning to FIG. 1, ring electrode 24 and tip electrode 26 may be paired together and coupled to an R-wave sense amplifier to detect the occurrence of an R-wave, and ring electrode 24 and subcutaneous housing electrode 20 or one of the C/D electrodes 22, 28 and 32 may be paired together for sensing the EGM signal. Alternatively, pace/sense electrodes 24 and 26 may be used for both R-wave detection and EGM sensing. Moreover, two of the C/D electrodes 32, 22 and 28 may be paired together for sensing the EGM signal.

The ICD IPG 10 preferably comprises an ICD operating system as depicted in FIG. 2 that provides the operating modes and functions of the MEDTRONIC® GEM 7227 single chamber ICD IPG, for example, that is programmable in operating mode and parameter values and is interrogatable employing the MEDTRONIC® Model 9790C external programmer 40, for example. FIG. 2 is a functional block diagram illustrating such a single chamber ICD operating system 100 that is merely exemplary of a variety of single chamber and dual chamber ICD systems having all or some of the capabilities described above in which the VT/VF discrimination functions of the present invention can be advantageously implemented. Moreover, the present invention can be incorporated in an implantable monitor having selected components of the operating system of FIG. 2.

The programming of ICD operating modes and parameters or the interrogation of data stored in the ICD IPG 10 or the initiation of UT transmission of the real time cardiac EGM is accomplished or initiated via programming or interrogation commands transmitted in a DT transmission by programmer 40 from the external telemetry antenna 42 to an ICD telemetry antenna 36 shown in FIG. 2. In the context of the present invention, the ICD operating system stores VT/VF detection episode data and VF delivery data that can be UT transmitted to the external programmer 40 for review by a physician. The ICD IPG telemetry system decodes the commands in the DT transmission, retrieves and formats the responsive data or cardiac EGM and conveys it to the external programmer 40 as an UT transmission in any of the manners known in the art.

The ICD system 100 includes one of more ICs typically mounted on one or more hybrid circuit, a PC board mounting a number of discrete components, and further large scale, discrete components. The heart of the ICD operating system is in hardware and software in the microcomputer based timing and control system IC 102 that is coupled with the other system blocks. The system IC 102 comprises the typical components of a microcomputer with operating algorithms maintained in memory or embedded in firmware and further operating system control circuitry that is conveniently located with it. Various depicted signal and control lines interconnecting these blocks, but not all are shown for simplicity of illustration and because they play no material role in the practice of the present invention.

The large scale, discrete, off-board, components illustrated in FIG. 2 include one or more batteries 136, HV output capacitors 138, 140, and (optionally) housing mounted, patient alert sound transducers 129 and/or activity sensors 134. The discrete components mounted to the PC board include telemetry antenna 36, reed switch 130, crystal 132, a set of HV discrete components of the HV C/D output circuitry 108, and switching and protection circuit components of isolation, protection and electrode selection circuitry 114. These discrete components are coupled to system IC 102 through other ICs and hybrid circuits incorporating the functional blocks 104–128 and 176 described further below. A similar ICD operating system to that depicted in FIG. 2 in which the present invention can be implemented is disclosed, for example, in the above-referenced '316 and '535 patents. The depicted functional blocks and discrete components of FIG. 2 can be arranged as part of one or two LV hybrid circuits, a HV hybrid circuit and a discrete component PC board. However, it will be understood that a single hybrid circuit could be employed that incorporates and supports all of the system ICs.

The exemplary ICD operating system 100 of FIG. 2 is powered by the battery 136 coupled to power supplies in power source block 106 for developing regulated high and low voltage power supplies Vhi and Vlo that are supplied to selected ones of the other functional blocks. Preferably, battery 136 is a lithium silver vanadium battery that can be employed to provide HV capacitor charging current and that produces a voltage from about 3.2 volts when fresh to about 2.5 volts at specified end of service for a single chamber ICD and twice these values for a dual chamber ICD. Power supply 106 also includes a power-on-reset (POR) circuit that generates a POR signal initially when the battery 136 is connected with power supply 106 and any time that the voltage of battery 136 does not meet a threshold voltage.

The crystal oscillator circuit 120 is coupled to clock crystal 132 and provides one or more system XTAL clock that is applied to the microcomputer-based control and timing system IC and distributed to other blocks of FIG. 2 as appropriate.

The telemetry I/O circuit 124 coupled with the IPG telemetry antenna 36 includes a UT transmitter that receives formatted UPLINK signals for uplink transmission and a DT receiver that receives and forwards DOWNLINK signals to telemetry I/O registers and control circuitry in system IC 102. In one telemetry scheme known in the art, the telemetry I/O circuit 124 is enabled to receive and decode DT interrogation and programming commands when the reed switch circuit provides the RS signal upon closure of reed switch 130 by an external programming head magnetic field. Downlink telemetry RF signals ring an L-C tank circuit including the IPG telemetry antenna 36. Other pacing functions are also affected when a magnetic field closes the reed switch 130 and the RS signal is generated in a manner well known in the art. In more recent telemetry schemes, the reed switch is not employed to receive DT transmissions and the telemetry antenna can be physically located outside the hermetically sealed enclosure. The components, operating modes and type of telemetry scheme employed in FIGS. 1 and 2 are not material to the present invention.

Optionally, a rate response circuit 122 is coupled to a physiologic activity sensor 134, which is preferably a transducer or accelerometer mounted to the IPG housing inner surface and provides activity correlated output signals to the rate response circuit 122 in a manner well known in the art. The rate response circuit 122 develops a rate control parameter (RCP) that is used to vary a pacing escape interval to pace the heart at a rate that provides adequate cardiac output. The signal processing of the transducer output signal by the rate response circuit 122 can be programmed through rate response parameter commands to develop the RCP in a number of ways known in the art. The RCP associated with a detected VT/VF episode can also be stored in memory in the system IC 102 for UT transmission of the episode data to the external programmer 40 for analysis by the patient's attending physician.

Optionally, a patient alert driver circuit 166 is coupled to a sound emitting transducer 129, which is mounted adjacent to the interior surface of the IPG housing and is powered to emit audible warning signals in high urgency and low urgency tones to alert the patient of VF detection and imminent delivery of a C/D shock or of events or conditions of concern warranting physician intervention. The warnings that can be programmed into operation or programmed "off" include pace/sense and CV/DEFIB lead impedance out of range (too high or too low), low battery voltage, excessive charge time for charging the HV capacitors, all therapies in a programmed group of therapies exhausted for a given episode, and an indication of the number of shocks delivered in an episode".

The block diagram of FIG. 2 depicts six input/output terminals labeled V+, V−, I, HVA, HVB, and COMMC that represent the connector terminals within the IPG connector block 104 that can be coupled to lead connector elements and lead conductors extending to the respective electrodes 24, 26, 30, 22, 32, and 28. As noted above, the number of input/output terminals and associated electrodes can be reduced to the minimal number necessary to practice the present invention.

Electrode selection switches in the isolation, protection and electrode selection circuitry 114 selectively couple pairs of the six input/output terminals labeled V+, V−, I, HVA, HVB, and COMMC to the R-wave sense amplifier 126, the ventricular EGM amplifier 128 and the V-PACE pulse generator 112 in response to a corresponding sense/pace electrode selection command from the microcomputer-based control and timing system IC 102. The sense/pace electrode selection command is programmable by the patient's attending physician through use of the external programmer 40 as described above.

A ventricular pacing function operating in any of the ways that are well known in the art may or may not be included in a low cost, limited function prophylactic ICD as described above. When the V-PACE generator 112 is included as depicted in FIG. 2, it provides V-PACE pulses through the selected pace/sense electrode pair having a pulse width and pulse amplitude set by the programmed PPW/PPA commands in a VVI of VVIR pacing mode. A timer in the microcomputer-based control and timing system 102 times out a programmed VVI pacing escape interval or a VVIR pacing escape interval that varies as a function of the RCP output by the rate response circuit 122. A V-TRIG signal is generated by microcomputer-based control and timing system 102 when the VVI or VVIR escape interval times out and applied to the analog rate limit circuit 110, which inhibits erroneous triggering of pacing at an unacceptably high rate in a manner well known in the art. The acceptable V-TRIG signals are passed through the analog rate limit 110 and trigger the delivery of the V-Pace pulse by the V-PACE pulse generator 112. The VVI or VVIR escape interval is restarted by a VSENSE generated by the ventricular sense amplifier 126 in response to an R-wave.

In response to a programming command, the V-PACE pulse generator 112 can be coupled through the isolation, protection and electrode selection circuitry 114 to the V+, V− input/output terminals to be thereby coupled with the pace/sense electrodes 24 and 26 to provide bipolar RV pacing. Or, the V-PACE pulse generator 112 can be coupled through the isolation, protection and electrode selection circuitry 114 to the V− terminal to be thereby coupled with the pace/sense electrode 26 and any of the I, HVA, HVB, and COMMC input/output terminals to be thereby coupled with the respective electrodes 20, 22, 32, and 28 to provide unipolar RV pacing.

In one preferred example, the ventricular sense amplifier 126 is coupled through the isolation, protection and electrode selection circuitry 114 to the V+, V− terminals to be thereby coupled with the pace/sense electrodes 24 and 26 to provide bipolar RV sensing of R-waves. The ventricular sense amplifier 126 comprises a programmable gain, bandpass amplifier, a threshold setting circuit, and a comparator for comparing the bandpass filtered ventricular cardiac signal amplitude to the threshold. The sensitivity/threshold of the ventricular sense amplifier 126 stored in sensitivity register 176 is programmable by the patient's attending physician through use of the external programmer 40 as described above. The ventricular sense amplifier 126 generates the VSENSE signal when it is not blanked and the amplitude of QRS complex exceeds the ventricular sense threshold, which is typically during the rise of the R-wave. The inputs to the ventricular sense amplifier 126 are disconnected from the V+, V− terminals by opening blanking switches in isolation, protection and electrode selection circuitry 114 in response to and for the duration of a VBLANK signal generated by a ventricular blanking circuit in microcomputer-based control and timing system IC 102 upon delivery of a V-PACE pulse or a C/D shock.

Similarly, the ventricular EGM (VEGM) amplifier 128 is coupled through electrode selection switch circuits in isolation, protection and electrode selection circuitry 114 to a pair of the input/output terminals selected from input/output terminals V+, V−, I, HVA, HVB, and COMMC in response to a programmable VEGM vector electrode selection command. The VEGM amplifier 128 filters and amplifies the cardiac signals and provides the VEGM signals to ADC/MUX 104. In the ADC/MUX 104, the VEGM is continually sampled at a sampling frequency of 256 Hz, and the sampled analog signal values are digitized and provided as VEGM DATA to RAM memory registers or buffers in system IC 102 for temporary storage on a FIFO basis. The temporarily stored VEGM DATA are shifted into memory registers within system IC 102 when a tachyarrhythmia episode at least partially satisfying the VF detection criteria occurs as described further herein.

Such VEGM DATA can be stored for retrieval in an UT transmission in memory registers to provide programmable length VEGM strips preceding and following the detection of the arrhythmia and encompassing any delivery of a VF shock. Due to memory limitations, the stored VEGM DATA may be discarded and replaced each time a VT/VF episode is detected. However, historic episode logs can be compiled and incremented in RAM in system IC 102 that provide the date, time, type of episode, cycle length, duration, and identify the last stored EGM DATA.

The depicted HV C/D output circuit 108 is of the type described in the above-incorporated '316 and '535 patents comprising a DC-DC converter and a HV output or discharge circuit for discharging the charge on the HV output capacitor bank 138 and 140 through selected ones of the C/D electrodes 22, 28, 32 and 20 of FIG. 1. The DC-DC converter comprises a HV charging circuit, a discrete HV step-up transformer, and the HV output capacitor bank 138 and 140 coupled to the secondary transformer coils. The charge on the HV output capacitor bank 138 and 140 is selectively discharged through combinations of the leads coupled with the C/D electrodes 26, 30 and 32 of FIG. 1 via HV switches in the isolation, protection and electrode selection circuitry 114. In a prophylactic ICD of the type described above, the depicted HV C/D output circuit 108 develops a high energy, monophasic or biphasic, C/D shock that is delivered through a selected pair of the C/D electrodes 26, 30 and 32 of FIG. 1 via the HV switches in the isolation, protection and electrode selection circuitry 114.

The microprocessor within the microcomputer-based control and timing system 102 operates as an interrupt driven device, under control of software stored in ROM associated with microprocessor and responds to interrupts including the VSENSE output of the R-wave sense amplifier 126 and the time-out of the VVI or VVIR escape interval. Any necessary mathematical calculations to be performed by the microprocessor and any updating of the values or intervals controlled by pacer timing/control circuitry within the microcomputer-based control and timing system 102 take place following such interrupts. These calculations include those described in more detail below associated with the VF discrimination methods of the present invention.

As described above and in the above-referenced '316 patent, the typical VT and VF detection criteria that have been employed in commercially released ICDs of the type illustrated in FIGS. 1 and 2 employ a rate/interval based timing criterion and an NID frequency criterion as tachyarrhythmia detection criteria for detecting the presence of and distinguishing between ventricular tachyarrhythmias. To this end, the intrinsic ventricular heart rate is measured on a beat-to-beat basis by timing the R—R interval between successive VSENSE signals output by the R-wave sense amplifier 126. The R—R interval is compared to the interval ranges or thresholds established, typically by programming, for each of VF, fast VT, and slow VT.

The VF counter, fast VT counter, and slow VT counter function like FIFO shift registers having Y stages each set to "1" or "0" that can be implemented in hardware, firmware or software. Each time that a current R—R interval is shorter than an interval threshold, a "1", for example, is advanced into the first stage of the register, the contents of each stage is advanced to the next stage, and the "1" or "0" in the Yth stage is discarded. Similarly, each time that a current R—R interval is longer than an interval threshold, a "0", for example, is advanced into the first stage of the register, the contents of each stage is advanced to the next stage, and the "1" or "0" in the Yth stage is discarded. Thus, the count X of the corresponding VF counter, fast VT counter, or slow VT counter is "incremented" if a "1" is advanced into the initial stage of the register and a "0" is discarded from the Yth stage and "decremented" if a "0" is advanced into the initial stage of the register and a "1" is discarded from the Yth stage. The count X remains the same if the same bit value "1" or "0" is advanced into the initial stage of the register and is discarded from the Yth stage.

For example, the R—R interval is simultaneously compared to a programmed fibrillation detection interval (FDI), a programmed fast tachycardia interval (FTDI), and a programmed slow tachycardia detection interval (TDI). The FDI count $X_{VF}$ is incremented if the R—R interval is shorter than the FDI and a "0" is discarded from the Yth stage or remains the same if a "0" is discarded from the Yth stage. Similarly, a slow VT count $X_{VT}$ is incremented or remains the same in response to an R—R interval shorter than TDI but longer then the FTDI or the FDI, and a fast VT count $X_{FVT}$ is incremented or remains the same in response to an R—R interval longer than FDI but shorter than the FTDI.

The counts $X_{VF}$, $X_{FVT}$, and $X_{VT}$ that accumulate in the respective VF counter, fast VT counter, and slow VT counter may be used to signal detection of an associated tachyarrhythmia (VF, fast VT, or slow VT) when the count $X_{VF}$, $X_{FVT}$, or $X_{VT}$ reaches a predetermined value referred to herein as the "number of intervals required for detection" (NID). Each rate zone may have its own defined NID, for example "VFNID" for fibrillation detection, "FVTNID" for fast VT detection and "VTNID" for slow VT detection. Thus, VF is declared when $X_{VF}$=VFNID, fast VT is declared when $X_{FVT}$=FVTNID, and slow VT is declared when $X_{VT}$=VTNID.

The present invention is directed to increasing the specificity of detection of true VF episodes in instances when the VF detection criteria may be mistakenly met by fast VT or SVT, particularly due to rapidly conducted AF or AFL. The present invention can be practiced in the context of the exemplary ventricular ICD embodiment of FIGS. 1 and 2 when conventional VF detection criteria are met or about to be met and a C/D is to be delivered to the RV to convert the apparent VF to NSR. It will be appreciated that the particular details of implementation of the VF detection criteria are not of primary importance. Moreover, it will be appreciated that the above-described fast VT and slow VT detection criteria can be eliminated or altered in the implementation of a simple prophylactic ICD intended to simply deliver a C/D shock therapy upon detection of a true VF episode.

In accordance with the preferred embodiments of the present invention, the VF detection criteria are augmented when the VF detection criteria are met ($X_{VF}$=VFNID) or, preferably, in the process of being met ($0<X_{VF}<$VFNID) by examining the morphology of a running series of the y most recent QRS complexes employing WTC comparisons to determine morphologic stability or instability. For example, the examination of the morphologic stability is preferably commenced when $X_{VF}$ is less than (VFNID-y). At least selected ones of the WTC data of y sets of WTC data are then processed to determine a match count (MATCH-CNT) x of the y sets of WTC data that match one another within predetermined match percent tolerances.

If the MATCH-CNT x meets a match count threshold for morphologic stability, then it is assumed that at least x of the last y QRS complexes exhibit morphologic stability, suggesting that the most recent QRS complexes likely are due to monomorphic fast VT or SVT, and final declaration of VF and delivery of a C/D shock are prevented. VF is finally declared and delivery of a C/D shock is allowed only if the VF detection criteria are met ($X_{VF}$=VFNID) and if the MATCH-CNT x does not meet the match count threshold.

Figure 3:
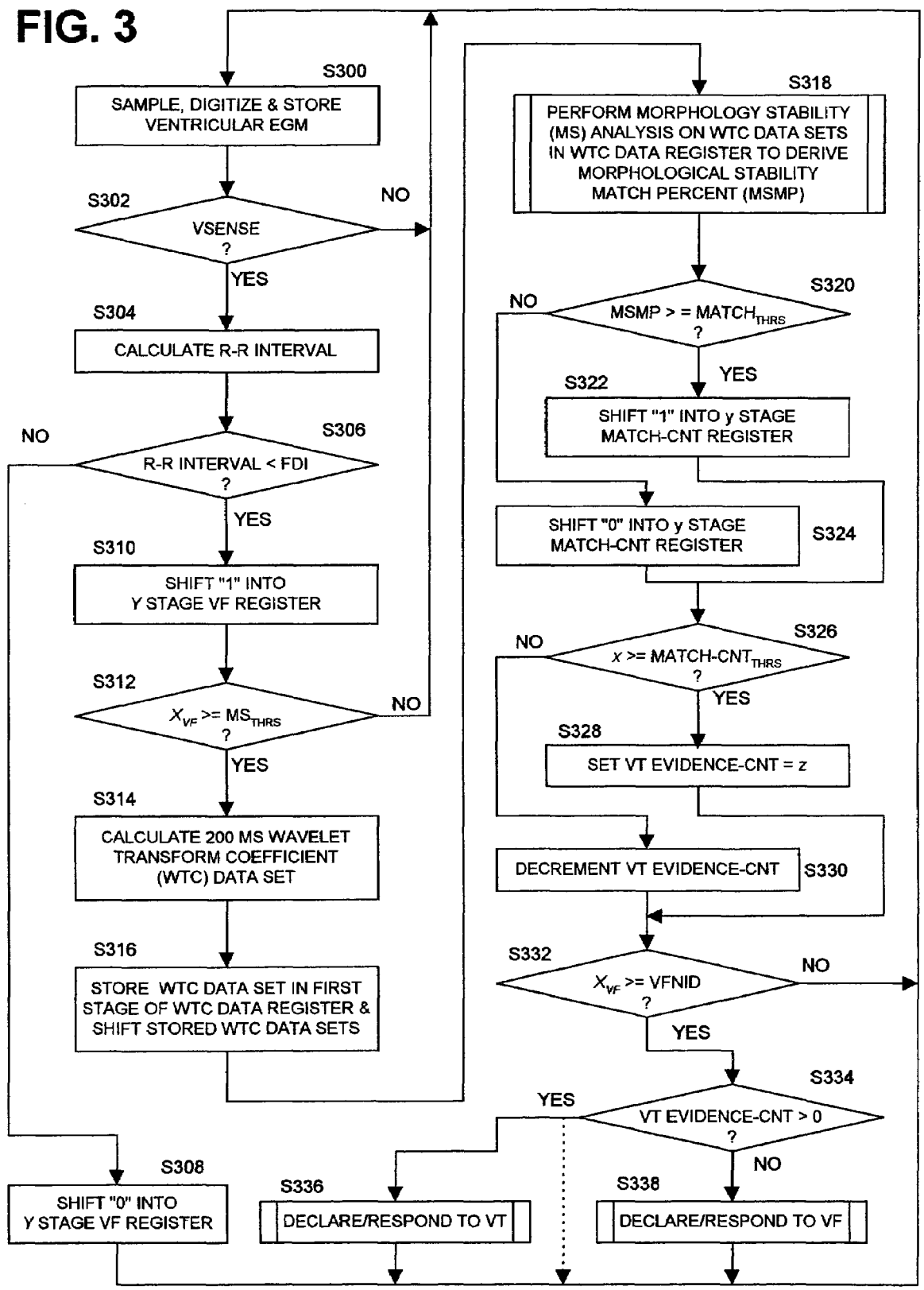
FIG. 3 is a flow chart illustrating a system and method of detecting and declaring a VF episode and providing a C/D shock therapy or monomorphic fast VT and providing an appropriate therapy in accordance with one embodiment of the present invention.

The above-described method can be employed in an ICD capable of providing a C/D shock therapy to counter VF and other appropriate therapies to counter VT. FIG. 3 depicts the steps of declaring that the ventricular tachyarrhythmia satisfying the conventional VF detection criteria is either a VF episode (or a polymorphic VT episode) or a monomorphic VT (or SVT) and delivering the programmed respective VF or VT therapy. In this illustrated method of FIG. 3, an evidence counter is set to a number z of QRS complexes when the MATCH-CNT x meets the match count threshold (indicating that x of the y QRS complexes exhibit morphologic stability). The evidence counter is decremented from z each time that the MATCH-CNT x does not meet the match count threshold. In this embodiment, if the VF detection criteria are met ($X_{VF}$=VFNID), but the evidence count exceeds zero (indicating that x of the y QRS complexes exhibit morphologic stability), then final declaration of VF is not made. Instead, VT is declared, and an appropriate VT therapy is delivered.

Figure 4:
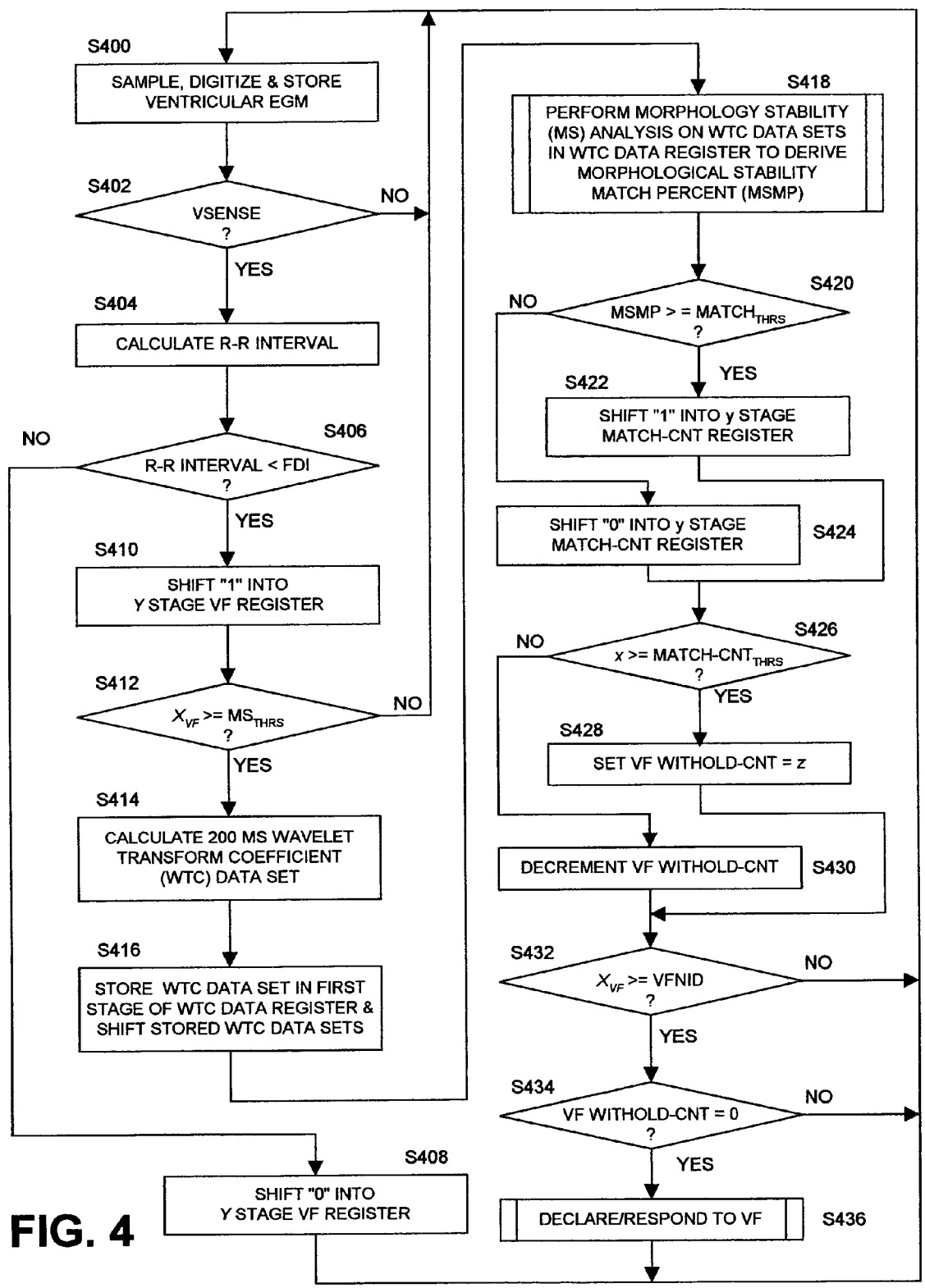
FIG. 4 is a flow chart illustrating a system and method of detecting and declaring a VF episode and providing a C/D shock therapy in accordance with a further embodiment of the present invention.

The method of FIG. 3 is preferably modified in the manner depicted in FIG. 4 to more stringently increase the specificity that a ventricular tachyarrhythmia is a true VF when the ICD is only capable of delivering a C/D shock therapy to counter VF. In this embodiment, if the VF detection criteria are met ($X_{VF}$=VFNID), but the MATCH-CNT x meets the match count threshold (indicating that x of the y QRS complexes exhibit morphologic stability), then final declaration of VF and delivery of the C/D shock is postponed while a further number z of QRS complexes are examined. The R—R intervals between ventricular sensed events and the morphologies of the further number z of QRS complexes are examined whereby the FDI count $X_{VF}$ and the MATCH-CNT x are updated on a beat-to-beat basis. The final declaration of VF and delivery of a C/D shock can only take place when the z R—R intervals and the z WTC data are compared, the VF detection criteria continue to be met ($X_{VF}$=VFNID), and the MATCH-CNT x no longer meets the match count threshold. The number z can be equal to or different than y. In a particular example, the VFNID is 18, Y=24, the match count threshold is 6, y=8, and z=8.

The methods of FIGS. 3 and 4 employ wavelet transform signal processing (e.g., the Haar wavelet transform), as illustrated in FIG. 5, to derive the WTC data sets and a selected one of the WTC algorithms described further below in reference to FIGS. 6–8 to distinguish polymorphic and monomorphic QRS complexes when VF detection criteria are satisfied.

Turning first to FIG. 3, in step S300, the EGM amplitude is continually sampled, digitized, and temporarily stored in a buffer on a FIFO basis employing the VEGM amplifier 128 and ADC/MUX 104 in a manner described in the above-referenced '519 patent, for example. A VSENSE event is declared in step S302 by the R-wave sense amplifier 126 or can be determined from the temporarily stored EGM amplitude data. The R—R interval is calculated in step S304 when each VSENSE is declared, and the R—R interval is compared to the FDI in step S306. In step S310, a "1" is shifted into the first stage of the VF counter, the data bits of the remaining stages are shifted one position, and the data bit in the Yth stage is discarded when the R—R interval is shorter than the FDI as determined in step S306. In step S308, a "0" is shifted into the first stage of the VF counter, the data bits of the remaining stages are shifted one position, and the data bit in the Yth stage is discarded when the R—R interval is longer than the FDI as determined in step S306. The VF count $X_{VF}$ can only be incremented when a "1" is shifted into the first stage of the VF counter and a "0" is shifted out of the Yth stage in step S310.

In a preferred example, there are 24 VF counter stages, and the VFNID is set to a lesser number, e.g., 18. The stages containing "1" bits are counted to derive the VF count $X_{VF}$. The VF count $X_{VF}$ is compared to a morphology stability test threshold ($MS_{THRS}$) in step S310, wherein $0<MS_{THRS}<VFNID$. As noted above, when VFNID=18 and y=8, the $MS_{THRS}$ can be set to 8 or to 10 (18–8), for example.

The determination and storage of WTC data sets commences in steps S314 and S316 when the VF count $X_{VF}$ meets the $MS_{THRS}$ as determined in step S312. In S314, EGM data collected in step S300 preceding and following the VSENSE event detected in step S302, e.g., a 200 ms window bracketing the VSENSE event, is subjected to WTC processing as illustrated in FIG. 5, to derive the WTC data set for the current QRS complex. Step S314 is repeated on each VSENSE event detected in step S302 and each time that the VF count $X_{VF}$ meets the $MS_{THRS}$ as determined in step S312. The current WTC data set calculated in step S314 is stored on a FIFO basis in the first stage of the WTC data register in step S316. The WTC data register would comprise two to at least y stages depending upon the particular morphology stability (MS) algorithm performed in step S314.

The MS analysis is performed in step S318 following one of the MS determination algorithms of the present invention depicted in FIGS. 5–8. Generally speaking, selected ones of the WTCs of the most recently derived, current, WTC data set are compared to the corresponding WTCs of either a selected WTC data set or WTC data sets or a mean of WTC data sets among y–1 stored WTC data sets. A MS match percent (MSMP) reflecting the degree of morphologic similarity of the current WTC data set to the referenced WTC data set or mean WTC values is determined by the particular MS determination method that is employed in step S318. The MSMP is compared to a match threshold ($MATCH_{THRS}$) in step S320. The MATCH-CNT x is incremented in step S322 if the MSMP meets the $MATCH_{THRS}$ in step S320. The MATCH-CNT x is decremented in step S324 if the MSMP does not meet the $MATCH_{THRS}$ in step S320.

The MATCH-CNT x is compared to a match count threshold ($MATCH\text{-}CNT_{THRS}$) in step S326. Thus, when a sustained run of R—R intervals shorter than the FDI occur, the steps S310–S326 can be repeated at least y times to derive a meaningful MATCH-CNT x. In step S328, an evidence counter is set to a number z of QRS complexes when the MATCH-CNT x meets the $MATCH\text{-}CNT_{THRS}$ in step S326. The evidence counter is decremented from z in step S330 each time that the MATCH-CNT x does not meet the $MATCH\text{-}CNT_{THRS}$ in step S326. If the VF detection criteria are met ($X_{VF}$=VFNID) in step S332, but the VT EVIDENCE-CNT exceeds zero (indicating that x of the y QRS complexes exhibit morphologic stability) as determined in step S334, then final declaration of VF is not made in step S338. Instead, VT is declared, and an appropriate VT therapy is delivered in step S336.

Thus, if both conditions of steps S332 and S334 are satisfied, then the ventricular tachyarrhythmia is finally declared to be a monomorphic fast VT. A fast VT therapy, e.g., a burst pacing therapy, may be delivered in step S336. It should be noted that in this algorithm of FIG. 3, further conventional morphological processing is preferably conducted to discriminate SVT and VT so that such fast VT therapies are not delivered to the ventricles during an SVT episode.

The ventricular tachyarrhythmia is declared to be VF and a C/D therapy is delivered in step S338 when the VF count $X_{VF}$ meets the VFNID as determined in step S332 and when the VT EVIDENCE-CNT exceeds zero as determined in step S334.

In practice, the FDI, the VFNID and one or both of the $MATCH_{THRS}$ and the $MATCH\text{-}CNT_{THRS}$ can be varied by programming to optimize the specificity of discrimination of true VF episodes in a given patient. Moreover, ventricular tachyarrhythmia termination algorithms are followed to determine whether a delivered therapy has terminated the episode. A C/D shock is typically delivered if the episode is not terminated by a delivered VT therapy.

The method of FIG. 3 could be employed in a prophylactic ICD not having the capability of delivering a VT therapy in step S336 as indicated by the dashed line back to step S300. However, it may be desirable to apply more rigorous criteria before delivery of a C/D shock therapy is allowed as shown in FIG. 4. In FIG. 4, steps S400–S426 are functionally equivalent to steps S300-S326 of FIG. 3 as described above. A withhold delay corresponding to a VF withhold count (VF WITHOLD-CNT) of z VSENSE events is effectively turned on in step S428 when the MATCH-CNT x does meet the MATCH-CNT$_{THRS}$ as determined in step S426 before the VF count $X_{VF}$ meets the VFNID as determined in step S432. In step S426, the MATCH-CNT x is compared to the MATCH-CNT$_{THRS}$, and the VF WITHOLD-CNT is set to z in step S428 when the MATCH-CNT x meets the MATCH-CNT$_{THRS}$. In that circumstance, the C/D shock therapy cannot be delivered until the WITHOLD-CNT is decremented from z back to zero in step S430 and the VF count $X_{VF}$ still or again meets the VFNID as determined in step S432. The withhold delay z can additionally be programmed to optimize the specificity of discrimination of true VF episodes in a given patient.

Thus, if the VF WITHOLD-CNT is set to z in step S428, then on each subsequent repetition of steps S402–S424, the VF WITHOLD-CNT is decremented each time that the MATCH-CNT x does not meet the MATCH-CNT$_{THRS}$ as determined in step S426 or the VF WITHOLD-CNT is reset back to z each time that the MATCH-CNT x does meet the MATCH-CNT$_{THRS}$ as determined in step S426. During this process, the VF count $X_{VF}$ can be incremented or decremented in steps S408 or S416. The ventricular tachyarrhythmia is declared to be VF and a C/D therapy is delivered in step S436 only when the VF count $X_{VF}$ meets the VFNID as determined in step S432 and when the VF WITHOLD-CNT is decremented to zero as determined in step S434. In practice, it would be expected that these steps would be met quickly during a true VF and that declaration and delivery of the C/D shock in step S436 would not be unduly delayed.

Turning to FIG. 5, it schematically depicts the application of a Haar wavelet transform to time sampled and digitized amplitude values of an analog electrogram to develop WTC data and the application of the inverse wavelet transform to the WTC data to reconstitute a representation of the analog EGM in a manner described in detail in the above-referenced '316 patent. The analog EGM is not necessarily reconstituted in the practice of the present invention. The wavelet coefficients are sorted by coefficient magnitude as shown in FIG. 5, and noise filtering can be accomplished by discarding the low magnitude WTCs as shown in FIG. 5. Only selected ones of the WTCs of each WTC data set are compared or otherwise processed in the MS algorithms of the present invention.

Figure 7:
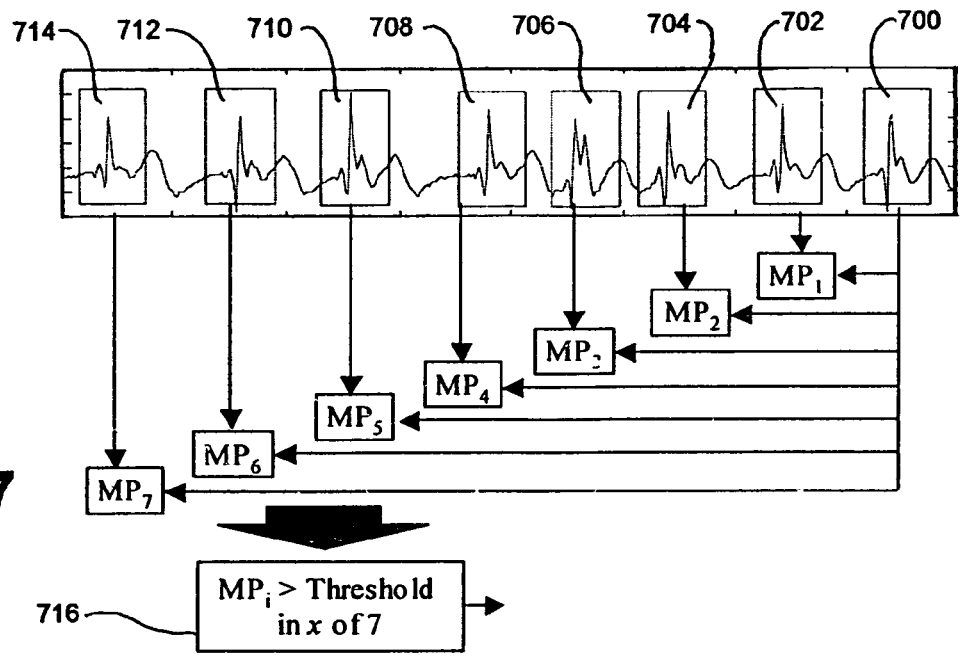
FIG. 7 is a graphical depiction of the mbMP algorithm that can be practiced in the flow chart of FIGS. 3 and 4.
Figure 8:
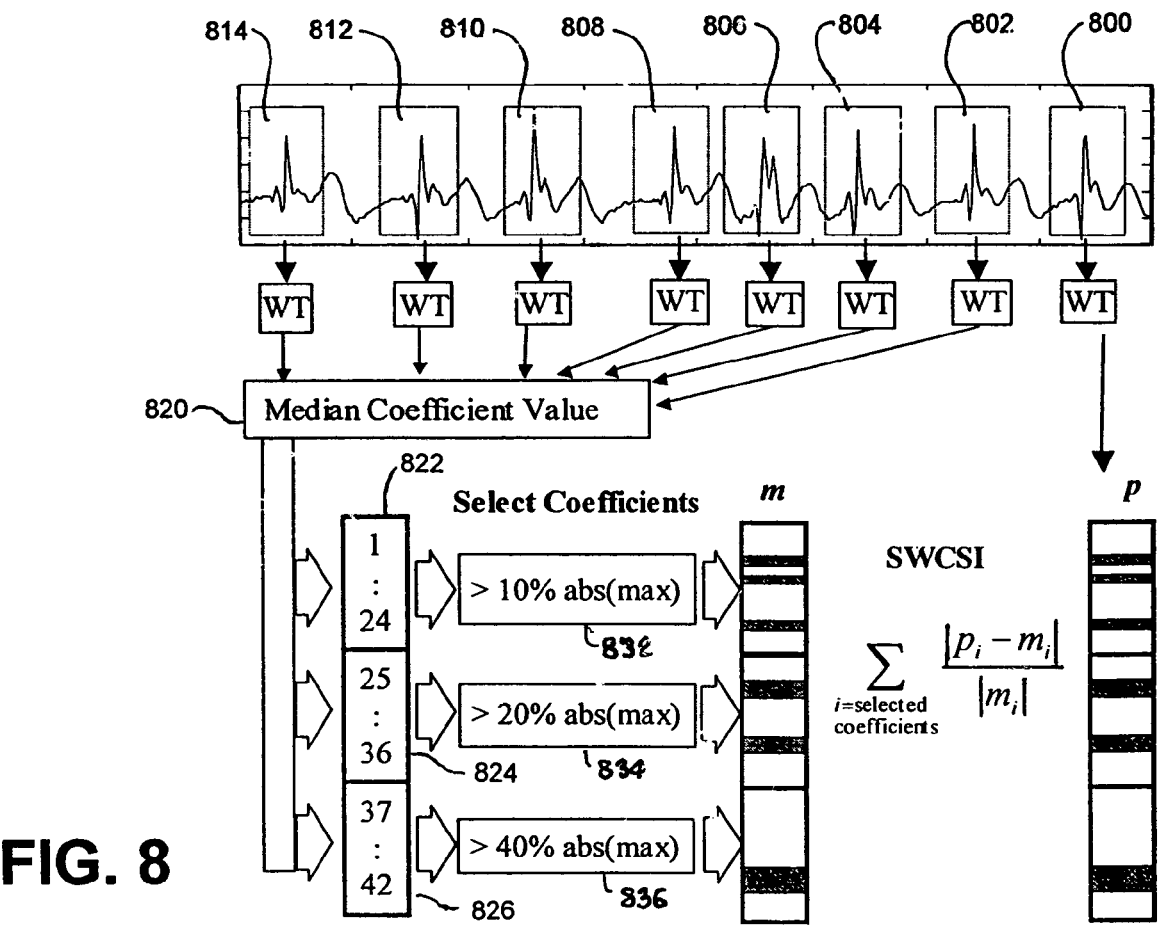
FIG. 8 is a graphical depiction of the SWCSI algorithm that can be practiced in the flow chart of FIGS. 3 and 4.

The MS algorithms of the present invention and certain of the steps of FIGS. 3 and 4 are schematically illustrated in FIGS. 6–8. In the 2 bMP algorithm depicted in FIG. 6, selected ones of the WTCs of the most recently derived, current, WTC data set are compared to the corresponding WTCs of a selected, previously derived and stored WTC data set to develop each MSMP, and the process is repeated y times to develop y MSMP values. In the mbMP algorithm depicted in FIG. 7, the WTCs of the current WTC data set are simultaneously compared to the corresponding WTCs of the preceding y-1 stored WTC data sets to simultaneously derive y-1 MSMP values. In the SWCSI algorithm depicted in FIG. 8, the WTCs of the current WTC data are subdivided into a plurality of WTC data sub-sets, and the WTCs of each WTC data sub-set are compared to corresponding mean WTCs of the corresponding WTC data sub-sets determined from the preceding y-1 stored WTC data sets. In each case the WTC data set comprises selected ones of 48 WTC points derived using the Haar wavelet illustrated in FIG. 5.

In FIG. 6, selected ones of the 48 point, ordered in magnitude, WTC data set of the current QRS complex 600 are compared to the corresponding selected ones of the 48 point, ordered in magnitude, WTC data set of a previous stored QRS complex 602. The selected ones of the WTC data sets are aligned to one another in block 604 and compared in step S606, and the MSMP is derived in block 606. The MSMP is compared to the MATCH$_{THRS}$ in steps S320 and S420 of FIGS. 3 and 4, respectively. It will be understood that the WTC data set of the current QRS complex 600 can be compared to a WTC data set of earlier previous stored QRS complex than the illustrated immediately preceding QRS complex 602. In this embodiment, y comparisons are successively made to develop the MS MATCH-CNT x of y to be tested in steps S328 and S426.

In FIG. 7, selected ones of the 48 point, ordered in magnitude, WTC data set of the current QRS complex 700 are simultaneously aligned and compared to each of the corresponding selected ones of the 48 point, ordered in magnitude, WTC data sets of seven (when y=8) previous stored QRS complexes 702, 704, 706, 708, 710, 712, 714. Thus, seven MSMP values, $MP_1$–$MP_7$, are simultaneously determined to compare to the MATCH$_{THRS}$ in steps S320 and S420 to determine the MS MATCH-CNT x that can be compared to the MATCH-CNT$_{THRS}$ in steps S328 and S426.

Frequency content information, in addition to morphologic stability, is incorporated as discriminatory information in the SWCSI algorithm illustrated in FIG. 8. This is achieved by considering selected raw WTC values within defined "scales" of the WTC data sets of seven (when y=8) previous stored QRS complexes 802, 804, 806, 808, 810, 812, 814 for performing a match percent like computation with respect to the WTC data set of the current QRS complex 800 to derive an SWCSI metric value that is used as the MSMP in step S320 of FIG. 3 or step S420 of FIG. 4.

In reference again to FIG. 5, in this case the number of wavelet coefficients equals 48, but only the coefficients 1–42 are employed since the coefficients become less useful in discrimination as they become wider or "coarser". For example, a set of m median WTC magnitudes 1–42 are determined in block 820 from seven (when y=8) previous WTC data sets 802–814 of WTC magnitudes 1–48. The comparable set of p, where p=m, current WTC magnitudes 1–42 are derived for the current QRS complex 800. The 42 median WTC magnitudes are ordered into scales 822, 824 and 826 shown in FIG. 8 comprising median WTC data points 1–24, 25–36 and 37–42, respectively, for example.

For each scale 822, 824 and 826, a defined percentage of the absolute maximum magnitude median WTC is used as a scale threshold for selecting one or more WTC of that scale to be combined with the equivalent one or more WTC of the current WTC data set. The scale threshold 832 is set at 10% of the absolute maximum median WTC magnitude within the finest scale 822 comprising coefficients 1 to 24. The scale threshold 834 is set at 20% of the absolute maximum median WTC magnitude within the coarser scale 824 comprising coefficients 25 to 36. The scale threshold 836 is set at 40% of the absolute maximum median WTC magnitude within the coarsest scale 824 comprising coefficients 37 to 42. The scale thresholds 832, 834, 836 are increased for each scale 822, 824, 826 in order to winnow out less significant ones of the m median WTC magnitudes for computation with the like numbered ones of ones of the p WTC magnitudes of the current WTC data set and to reduce the resulting computational complexity without appreciably decreasing specificity.

In this way, a subset of the set m is determined comprising the median WTC magnitudes $m_i$ or data points within the three scales 822, 824, and 826 having magnitudes exceeding the respective 10% abs(max) scale threshold, the 20% abs(max) scale threshold, and the 40% abs(max) scale threshold. A subset of the current WTC data set p is determined comprising the corresponding (in WTC number i) WTC magnitudes $p_i$. The selected median and current WTC subset magnitudes $m_i$ and $p_i$ are then used to compute an SWCSI metric value to be used as the MS MATCH-CNT x in FIG. 3 or FIG. 4 by:

$$SWCSI = \sum_{\substack{i=selected \\ coefficients}} \frac{|p_i - m_i|}{|m_i|}$$

In these embodiments of FIGS. 7 and 8, it is therefore necessary to store the seven previous WTC data sets on a FIFO basis while the respective algorithm is performed each time that a new WTC data set is accumulated when the VF count $X_{VF}$ meets the $MS_{THRS}$ to determine the MS MATCH-CNT x. The repeated processing of the algorithms continues as long as the VF count $X_{VF}$ meets the $MS_{THRS}$, the MS MATCH-CNT x does not meet the MATCH-CNT$_{THRS}$ and the VF count $X_{VF}$ still or again meets the VFNID. Moreover, the processing continues in accordance with the algorithm of FIG. 4 as long as the VF WITHOLD-CNT z exceeds zero.

Although the preferred embodiments described above relate to the discrimination of ventricular tachyarrhythmias, it will be understood that the principles of the present invention may be applied to discrimination of atrial tachyarrhythmias. For example, in practice within atrial or dual chamber ICDs, the near or far field atrial EGM and atrial sense events can be determined, AF detection criterion can be defined, and an AF episode or atrial tachyarrhythmia (AT) can be provisionally declared following the steps S300–S312 of FIG. 3 or S400–S412 of FIG. 4 or employing any other known AF detection criteria. The algorithm of FIG. 6 can be employed to determine an MSMP of the atrial EGM for use in the algorithms of FIG. 3 or FIG. 4 for discrimination between AF and organized AT. ATP therapies will be delivered for organized atrial tachyarrhythmias only, and CD/shock therapy may or may not be applied for AF detection. So, FIG.4 applies to the case when only ATP therapies need to be delivered for organized AT and ATP therapy needs to be withheld for AF or disorganized AT. The step S420 comparison can be reversed to perform an ATP therapy withhold if evidence for AF or disorganized AT is found when the MSMP<MATCH$_{THRS}$. Therefore, it will be understood that the present invention can be applied in discrimination of both atrial and ventricular tachyarrhythmias in the manner described herein.

Further, the present invention is adaptable and applicable to subcutaneous sensing and detection of arrhythmias.

Moreover, it will be appreciated that the present invention may be practiced in contexts that do not rely upon the provisional declaration of a polymorphic tachyarrhythmia, e.g., AF or VF, following steps S304–S312 and step S332 of FIG. 3 or steps S404–S412 and step S432 of FIG. 4. The algorithm of FIG. 6 can be employed with the remaining steps of FIGS. 3 or 4 to make the determinations of steps S336 and S338 or step S436, respectively, based upon the results of step S334 or step S434, respectively. Such a simplified algorithm can be advantageously applied in discrimination of both atrial and ventricular tachyarrhythmias in the manner described herein.

All patents and publications referenced herein are hereby incorporated by reference in their entireties.

It will be understood that certain of the above-described structures, functions and operations of the above-described preferred embodiments are not necessary to practice the present invention and are included in the description simply for completeness of an exemplary embodiment or embodiments.

In addition, it will be understood that specifically described structures, functions and operations set forth in the above-referenced patents can be practiced in conjunction with the present invention, but they are not essential to its practice. It is therefore to be understood, that within the scope of the appended claims, the invention may be practiced otherwise than as specifically described without actually departing from the spirit and scope of the present invention.

One skilled in the art will appreciate that the present invention can be practiced with embodiments other than those disclosed. The disclosed embodiments are presented for purposes of illustration and not limitation, and the present invention is limited only by the claims that follow.

What is claimed is:

1. In an implantable medical device that detects a polymorphic tachyarrhythmia of the heart of a patient as a function of measured time intervals between sensed events in a cardiac signal, a method of improving the specificity of discriminating between a monomorphic tachyarrhythmia and a polymorphic tachyarrhythmia comprising the steps of:
   a) provisionally declaring a polymorphic tachyarrhythmia when at least a first number of the measured time intervals satisfy the polymorphic tachyarrhythmia detection criteria;
   b) successively sampling, processing, and temporarily storing the cardiac signals to derive a plurality y of data sets of signal amplitudes;
   c) successively deriving a plurality y of sets of wavelet transform coefficients from the respective plurality y of data sets of signal amplitudes;
   d) comparing at least selected ones of the wavelet transform coefficients of each of the y sets of wavelet transform coefficients to determine a match count x of the y sets of wavelet transform coefficients that match one another within at least a predetermined match tolerance;
   e) withholding the final declaration of a polymorphic tachyarrhythmia if the match count x indicates that the corresponding cardiac signals exhibit morphologic stability suggestive of a monomorphic tachyarrhythmia; and
   f) making the final declaration of a polymorphic tachyarrhythmia if the match count x indicates that the corresponding cardiac signals exhibit morphological instability suggestive of a polymorphic tachyarrhythmia and the polymorphic tachyarrhythmia is provisionally declared in step a).

2. The method of claim 1, further comprising repeating steps b) through f) as long as step a) is met until step f) is met.

3. The method of claim 2, wherein the implantable medical device further comprises an implantable cardioverter/defibrillator having the capability of delivering a C/D shock therapy and further comprising:
  g) delivering a C/D shock therapy when the final declaration of a polymorphic tachyarrhythmia is made in step f).

4. The method of claim 2, wherein step e) comprises:
  establishing a withhold count corresponding to z measured time intervals between sensed events of successive cardiac signals; and
  repeating steps a) through d) at least z times.

5. The method of claim 2, wherein the implantable medical device further comprises an implantable cardioverter/defibrillator having the capability of delivering a C/D shock therapy and wherein:
  step e) comprises establishing a withhold count corresponding to z measured time intervals between sensed events of successive cardiac signals; and
  further comprising:
  g) repeating steps a) through d) at least z times; and
  h) delivering a C/D shock therapy when the final declaration of a polymorphic tachyarrhythmia is made in step f).

6. The method of claim 2, wherein the implantable medical device further comprises an implantable cardioverter/defibrillator having the capability of delivering a C/D shock therapy and delivering an anti-tachycardia therapy and further comprising:
  g) delivering a C/D shock therapy when the final declaration of a polymorphic tachyarrhythmia is made in step f); and
  h) delivering an anti-tachycardia therapy when the match count x indicates that the corresponding cardiac signals exhibit morphologic stability suggestive of a monomorphic tachyarrhythmia in step e) and a polymorphic tachyarrhythmia is provisionally declared in step a).

7. The method of claim 1, wherein the implantable medical device further comprises an implantable cardioverter/defibrillator having the capability of delivering a C/D shock therapy and delivering an anti-tachycardia therapy and further comprising:
  k) delivering a C/D shock therapy when the final declaration of a polymorphic tachyarrhythmia is made in step f); and
  l) delivering an anti-tachycardia therapy when the match count x indicates that the corresponding cardiac signals exhibit morphologic stability suggestive of a monomorphic tachyarrhythmia in step e) and a polymorphic tachyarrhythmia is provisionally declared in step a).

8. The method of claim 1, wherein:
  step b) further comprises framing a sample data set of signal amplitude values as a data frame related to the detection of a feature of interest of the cardiac signal; and
  step c) further comprises wavelet transforming the data frame of signal amplitude values to generate a set of wavelet transform coefficients.

9. The method of claim 1, wherein step d) comprises:
  comparing at least certain wavelet transform coefficients of the most recent set of wavelet transform coefficients among the plurality y of sets of wavelet transform coefficients to at least certain wavelet transform coefficients of the preceding (y−1) sets of wavelet transform coefficients and determining (y−1) match values representing the degree that the compared wavelet coefficients of the most recent set match the wavelet transform coefficients of the (y−1) sets;
  comparing each of the (y−1) match values to a match count threshold; and
  determining the match count x of the (y−1) match values that meet the match count threshold.

10. The method of claim 9, wherein:
  step d) comprises comparing the match count x to a morphologic stability match count threshold; and
  step e) comprises withholding the final declaration of a polymorphic tachyarrhythmia if the match count x meets the morphologic stability match count threshold.

11. The method of claim 10, wherein step f) comprises making the final declaration of a polymorphic tachyarrhythmia if the match count x does not meet the morphologic stability match count threshold and a polymorphic tachyarrhythmia is provisionally declared in step a).

12. The method of claim 10, wherein step e) comprises:
  establishing a withhold count corresponding to z measured time intervals between sensed events of successive cardiac signals; and
  repeating steps a) through d) at least z times.

13. The method of claim 9, wherein step f) comprises making the final declaration of a polymorphic tachyarrhythmia if the match count x does not meet the morphologic stability match count threshold and a polymorphic tachyarrhythmia is provisionally declared in step a).

14. The method of claim 1, wherein step d) comprises:
  each time that step c) is performed to derive the most recent set of wavelet coefficients, comparing at least certain wavelet transform coefficients of the most recent set of wavelet transform coefficients to at least certain wavelet transform coefficients of a selected preceding set of wavelet transform coefficients and determining a match value representing the degree that the compared wavelet coefficients of the most recent set match the wavelet transform coefficients of the preceding set;
  accumulating y match values;
  comparing each of the y match values to a match count threshold; and
  determining the match count x of the y match values that meet the match count threshold.

15. The method of claim 14, wherein step e) comprises:
  comparing the match count x to a morphologic stability match count threshold; and
  withholding the final declaration of a polymorphic tachyarrhythmia if the match count x meets the morphologic stability match count threshold.

16. The method of claim 15, wherein step f) comprises making the final declaration of a polymorphic tachyarrhythmia if the match count x does not meet the morphologic stability match count threshold and a polymorphic tachyarrhythmia is provisionally declared in step a).

17. The method of claim 15, wherein step e) comprises:
  establishing a withhold count corresponding to z measured time intervals between sensed events of successive cardiac signals; and
  repeating steps a) through d) at least z times.

18. The method of claim 14, wherein step f) comprises:
  comparing the match count x to a morphologic stability match count threshold; and
  making the final declaration of a polymorphic tachyarrhythmia if the match count x does not meet the morphologic stability match count threshold and a polymorphic tachyarrhythmia is provisionally declared in step a).

19. The method of claim 1, wherein step d) comprises:
determining m median wavelet transform coefficient magnitudes from the wavelet transform coefficients in each of (y−1) wavelet transform coefficient data sets preceding, in time, a current wavelet transform coefficient data set having p wavelet transform coefficient magnitudes;
ordering the set m of the median wavelet transform coefficient magnitudes into a plurality of scales;
comparing the median wavelet transform coefficient magnitudes in each scale to a scale threshold of the scale to derive a subset of median wavelet transform coefficient magnitudes $m_i$ that meet the scale thresholds;
determining a subset of current wavelet transform coefficient magnitudes $p_i$ each corresponding in wavelet number to the wavelet numbers of the subset of median wavelet transform coefficient magnitudes $m_i$; and
deriving a selective wavelet coefficient stability index (SWCSI) to be employed as the match count x in steps e) and f) by:

$$SWCSI = \sum_{\substack{i=selected \\ coefficients}} \frac{|p_i - m_i|}{|m_i|}.$$

20. The method of claim 19, further comprising determining the scale threshold of each scale as a percentage of the absolute maximum median wavelet transform coefficient magnitude in the scale.

21. In an implantable medical device that provisionally detects a polymorphic tachyarrhythmia of the heart of a patient as a function of measured time intervals between sensed events in a cardiac signal, a system of improving the specificity of discriminating between a monomorphic tachyarrhythmia and a polymorphic tachyarrhythmia comprising:
provisional declaring means for provisionally declaring a polymorphic tachyarrhythmia when at least a first number of the measured time intervals satisfy the polymorphic tachyarrhythmia detection criteria;
signal processing means for successively sampling, processing, and temporarily storing the cardiac signals to derive a plurality y of data sets of signal amplitudes;
wavelet transform means for successively deriving a plurality y of sets of wavelet transform coefficients from the respective plurality y of data sets of signal amplitudes;
comparing means for comparing at least selected ones of the wavelet transform coefficients of each of the y sets of wavelet transform coefficients to determine a match count x of the y sets of wavelet transform coefficients that match one another within at least a predetermined match tolerance;
withholding means for withholding the final declaration of a polymorphic tachyarrhythmia if the match count x indicates that the corresponding cardiac signals exhibit morphologic stability suggestive of a monomorphic tachyarrhythmia; and
final declaring means for making the final declaration of a polymorphic tachyarrhythmia if the match count x indicates that the corresponding cardiac signals exhibit morphological instability suggestive of a polymorphic tachyarrhythmia and the polymorphic tachyarrhythmia is provisionally declared.

22. The system of claim 21, wherein the implantable medical device further comprises an implantable cardioverter/defibrillator having the capability of delivering a C/D shock therapy and further comprising:
means for delivering a C/D shock therapy when the final declaration of a polymorphic tachyarrhythmia is made.

23. The system of claim 22, wherein:
the withholding means further comprises:
means for establishing a withhold count corresponding to z measured time intervals between sensed events of successive cardiac signals if the match count x indicates that the corresponding cardiac signals exhibit morphologic stability; and
means for decrementing the withhold count each time that a match count x indicates that the corresponding cardiac signals exhibit morphological instability suggestive of a polymorphic tachyarrhythmia; and
the final declaring means further comprises means responsive to the withhold count for declaring a polymorphic tachyarrhythmia only when the withhold count is decremented to a withhold count less than z.

24. The system of claim 21, wherein:
the withholding means further comprises:
means for establishing a withhold count corresponding to z measured time intervals between sensed events of successive cardiac signals if the match count x indicates that the corresponding cardiac signals exhibit morphologic stability; and
means for decrementing the withhold count each time that a match count x indicates that the corresponding cardiac signals exhibit morphological instability suggestive of a polymorphic tachyarrhythmia; and
the final declaring means further comprises means responsive to the withhold count for declaring a polymorphic tachyarrhythmia only when the withhold count is decremented to a withhold count less than z.

25. The system of claim 21, wherein the implantable medical device further comprises an implantable cardioverter/defibrillator having the capability of delivering a C/D shock therapy and delivering an anti-tachycardia therapy and further comprising:
means for delivering a C/D shock therapy when the final declaration of a polymorphic tachyarrhythmia is made; and
means for delivering an anti-tachycardia therapy when the match count x indicates that the corresponding cardiac signals exhibit morphologic stability suggestive of a monomorphic tachyarrhythmia and a polymorphic tachyarrhythmia is provisionally declared.

26. The system of claim 21, wherein:
the signal processing means further comprises means for framing a sample data set of signal amplitude values as a data frame related to the detection of a feature of interest of the cardiac signal; and
the wavelet transform means further comprises wavelet transforming the data frame of signal amplitude values to generate a set of wavelet transform coefficients.

27. The system of claim 21, wherein the comparing means further comprises:
means for comparing at least certain wavelet transform coefficients of the most recent set of wavelet transform coefficients among the plurality y of sets of wavelet transform coefficients to at least certain wavelet transform coefficients of the preceding (y−1) sets of wavelet transform coefficients and determining (y−1) match values representing the degree that the compared wavelet coefficients of the most recent set match the wavelet transform coefficients of the (y−1) sets;

means for comparing each of the (y−1) match values to a match count threshold; and means for determining the match count x of the (y−1) match values that meet the match count threshold.

28. The system of claim 27, wherein the withholding means further comprises:

means for comparing the match count x to a morphologic stability match count threshold; and means for withholding the final declaration of a polymorphic tachyarrhythmia if the match count x meets the morphologic stability match count threshold.

29. The system of claim 28, wherein the final declaring means comprises means for making the final declaration of a polymorphic tachyarrhythmia if the match count x does not meet the morphologic stability match count threshold and a polymorphic tachyarrhythmia is provisionally declared.

30. The system of claim 27, wherein the final declaring means comprises means for making the final declaration of a polymorphic tachyarrhythmia if the match count x does not meet the morphologic stability match count threshold and a polymorphic tachyarrhythmia is provisionally declared.

31. The system of claim 27, wherein:

the withholding means further comprises:

means for establishing a withhold count corresponding to z measured time intervals between sensed events of successive cardiac signals if the match count x indicates that the corresponding cardiac signals exhibit morphologic stability; and means for decrementing the withhold count each time that a match count x indicates that the corresponding cardiac signals exhibit morphological instability suggestive of a polymorphic tachyarrhythmia; and the final declaring means further comprises means responsive to the withhold count for declaring a polymorphic tachyarrhythmia only when the withhold count is decremented to a withhold count less than z.

32. The system of claim 21, wherein the comparing means further comprises:

means for comparing at least certain wavelet transform coefficients of the most recent set of wavelet transform coefficients to at least certain wavelet transform coefficients of a selected preceding set of wavelet transform coefficients and determining a match value representing the degree that the compared wavelet coefficients of the most recent set match the wavelet transform coefficients of the preceding set;

means for accumulating y match values;

means for comparing each of the y match values to a match count threshold; and means for determining the match count x of the y match values that meet the match count threshold.

33. The system of claim 32, wherein the withholding means further comprises:

means for comparing the match count x to a morphologic stability match count threshold; and means for withholding the final declaration of a polymorphic tachyarrhythmia if the match count x meets the morphologic stability match count threshold.

34. The system of claim 33, wherein the final declaring means comprises means for making the final declaration of a polymorphic tachyarrhythmia if the match count x does not meet the morphologic stability match count threshold and a polymorphic tachyarrhythmia is provisionally declared.

35. The system of claim 32, wherein the final declaring means comprises means for making the final declaration of a polymorphic tachyarrhythmia if the match count x does not meet the morphologic stability match count threshold and a polymorphic tachyarrhythmia is provisionally declared.

36. The system of claim 32, wherein:

the withholding means further comprises:

means for establishing a withhold count corresponding to z measured time intervals between sensed events of successive cardiac signals if the match count x indicates that the corresponding cardiac signals exhibit morphologic stability; and means for decrementing the withhold count each time that a match count x indicates that the corresponding cardiac signals exhibit morphological instability suggestive of a polymorphic tachyarrhythmia; and the final declaring means further comprises means responsive to the withhold count for declaring a polymorphic tachyarrhythmia only when the withhold count is decremented to a withhold count less than z.

37. The system of claim 21, wherein the comparing means further comprises:

means for determining m median wavelet transform coefficient magnitudes from the wavelet transform coefficients in each of (y−1) wavelet transform coefficient data sets preceding, in time, a current wavelet transform coefficient data set having p wavelet transform coefficient magnitudes;

means for ordering the set m of the median wavelet transform coefficient magnitudes into a plurality of scales;

means for comparing the median wavelet transform coefficient magnitudes in each scale to a scale threshold of the scale to derive a subset of median wavelet transform coefficient magnitudes $m_i$ that meet the scale thresholds;

means for determining a subset of current wavelet transform coefficient magnitudes $p_i$ each corresponding in wavelet number to the wavelet numbers of the subset of median wavelet transform coefficient magnitudes $m_i$; and means for deriving a selective wavelet coefficient stability index (SWCSI) to be employed as the match count x by:

$$SWCSI = \sum_{\substack{i=selected \\ coefficients}} \frac{|p_i - m_i|}{|m_i|}.$$

38. The system of claim 37, further comprising means for determining the scale threshold of each scale as a percentage of the maximum median wavelet transform coefficient magnitude in the scale.

39. The system of claim 37, wherein the withholding means further comprises:

means for comparing the match count x to a morphologic stability match count threshold; and means for withholding the final declaration of a polymorphic tachyarrhythmia if the match count x meets the morphologic stability match count threshold.

40. The system of claim 39, wherein the final declaring means comprises means for making the final declaration of a polymorphic tachyarrhythmia if the match count x does not meet the morphologic stability match count threshold and a polymorphic tachyarrhythmia is provisionally declared.

41. The system of claim 37, wherein the final declaring means comprises means for making the final declaration of a polymorphic tachyarrhythmia if the match count x does not meet the morphologic stability match count threshold and a polymorphic tachyarrhythmia is provisionally declared.

42. The system of claim 37, wherein:

the withholding means further comprises:

means for establishing a withhold count corresponding to z measured time intervals between sensed events of successive cardiac signals if the match count x indicates that the corresponding cardiac signals exhibit morphologic stability; and means for decrementing the withhold count each time that a match count x indicates that the corresponding cardiac signals exhibit morphological instability suggestive of a polymorphic tachyarrhythmia; and the final declaring means further comprises means responsive to the withhold count for declaring a polymorphic tachyarrhythmia only when the withhold count is decremented to a withhold count less than z.

* * * * *